(12) United States Patent
Haap et al.

(10) Patent No.: US 7,964,633 B2
(45) Date of Patent: Jun. 21, 2011

(54) SULFONAMIDE DERIVATIVES

(75) Inventors: Wolfgang Haap, Loerrach (DE); Paul Hebeisen, Basel (CH); Eric A. Kitas, Aesch BL (CH); Philipp Christoph Kohler, Oberdorf SO (CH); Holger Kuehne, Grenzach-Wyhlen (DE); Armin Ruf, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 856 days.

(21) Appl. No.: 11/903,580

(22) Filed: Sep. 24, 2007

(65) Prior Publication Data
US 2008/0085928 A1    Apr. 10, 2008

(30) Foreign Application Priority Data
Sep. 29, 2006 (EP) .................... 06121544

(51) Int. Cl.
*A61K 31/381* (2006.01)
*C07D 409/12* (2006.01)
(52) U.S. Cl. ........................................ 514/444; 549/59
(58) Field of Classification Search .................. 514/444; 549/59
See application file for complete search history.

(56) References Cited

U.S. PATENT DOCUMENTS
3,607,935 A    9/1971    Hilmer et al.

FOREIGN PATENT DOCUMENTS
EP    0 542 556 A1    5/1993

OTHER PUBLICATIONS
King, Med. Chem.: Priciple and Practice (1994), pp. 206-208.*
* cited by examiner

*Primary Examiner* — Taofiq A Solola
(74) *Attorney, Agent, or Firm* — George W. Johnston; Dennis P. Tramaloni; Samuel H. Megerditchian

(57) ABSTRACT

Compounds of formula (I)

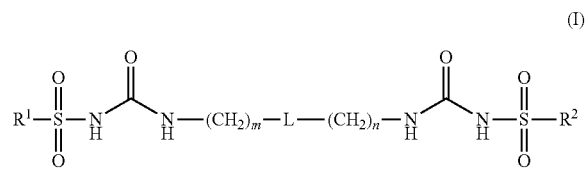

as well as pharmaceutically acceptable salts and esters thereof, wherein L, $R^1$, $R^2$, m and n have the meaning given in claim 1 and which can be used in the form of pharmaceutical compositions.

20 Claims, No Drawings

SULFONAMIDE DERIVATIVES

PRIORITY TO RELATED APPLICATION(S)

This application claims the benefit of European Patent Application No. 06121544.8, filed Sep. 29, 2006, which is hereby incorporated by reference in its entirety.

FIELD OF THE INVENTION

The present invention relates to novel sulfonamide derivatives which are useful as FBPase inhibitors.

The invention is concerned particularly with compounds of formula (I)

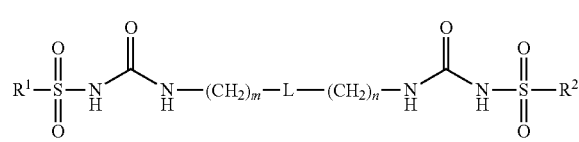

and pharmaceutically acceptable salts or esters thereof.

All documents cited to and/or relied upon below are expressly incorporated herein by reference.

BACKGROUND OF THE INVENTION

Fructose-1,6-bisphosphatase (FBPase) is a rate-limiting enzyme of gluconeogenesis that is allosterically regulated by AMP and responsible for the hydrolysis of Fructose-1,6-bisphosphate to Fructose-6-phosphate. FBPase AMP site inhibitors have valuable pharmacological properties suitable in both human and veterinary medicine.

Inhibitors of FBPase and of the production of Fructose-6-phosphate that is reversibly converted to Glucose-6-phosphate, a metabolite which represents a common precursor for diverse essential metabolic pathways generating glucose, glycogen, ATP, amino acids, nucleotides, NADPH and so forth, have a large variety of indications related to the management of body homeostasis and the prevention of metabolic dysfunctions. For example, inhibitors of FBPase and of gluconeogenesis in the liver, or in other organs capable of producing glucose like kidney or intestine, are hypoglycaemic agents and are indicated for the treatment and/or the prophylaxis of disorders of glucose homeostasis, such as Diabetes Mellitus, in particular Type II and Type I Diabetes Mellitus (NIDDM and IDDM), Impaired Fasting Glucose (IFG), Impaired Glucose Tolerance (IGT), and for the prevention of the progression of disorders of the Metabolic Syndrome (MetS, also described as Syndrome X or Insulin Resistance Syndrome) which most important components are insulin resistance (with or without IGT), obesity, dyslipidemia, hypertension, prothrombic and proinflammatory states. As such, compounds of the present invention are also indicated for the prevention and/or the treatment of diabetic complications or diabetic-associated diseases such as cardiomyopathy, macrovascular atherosclerotic disorders, including coronary, cerebrovascular and peripheral artery diseases, microvascular diseases including retinopathy, cataracts, blindness and nephropathy, neuropathy (peripheral neuropathy and sympathetic nerve disorders), diabetic necrosis, infection or depression, and so forth.

In addition, inhibitors of FBPase that cause the accumulation of Fructose-1,6-bisphosphate capable for increasing the glycolytic production of ATP have cytoprotective effects as anti-ischaemic agents and are useful for preventing ischaemia-induced tissue damage. Therefore, inhibitors of FBPase can be used in a variety of ischaemic and inflammatory conditions where acute management of tissue injury could be beneficial such as surgical trauma, myocardial infarction, congestive heart failure, stroke, sickle cell disease, and so forth, and have further utility in cardioprotection, in improving cardiac function and tolerance to exercise, in improving red-blood cells and pulmonary endothelial functions, in organ preservation in transplants, and so forth. As such, inhibitors of FBPase can also be used to treat asthma attacks, hypertension, atherosclerosis and so forth, and in the management of certain excess glycogen storage diseases such as McArdle disease (GSD-Type V) and others.

Also as inhibitors of FBPase, and thereby of the production from the gluconeogenic pathway of Fructose-6-phosphate and Glucose-6-phosphate that serve as precursors for other pathways of hexose metabolism (e.g. synthesis of aminosugars/hexosamines that are used for the biosynthesis of glycoproteins, glycosphingolipids or glycosaminoglycans, and uronic acid pathway that leads to glucuronate, a precursor of proteoglycans and conjugated glucuronides, and so forth), or for the pentose phosphate pathway (PPP, also called phosphogluconate pathway) which provides the carbon source for common aromatic biosynthetic pathways (nucleotides and amino-acids synthesis) and generates NADPH for reductive biosyntheses (lipogenesis, steroidogenesis), such inhibitors can have further utility in the prevention and/or the management of a large set of diseases including obesity, atherosclerosis, inflammation, Alzheimer disease, cancer or respiratory disorders such as excess mucus production and allergic asthma, excess surfactant synthesis, cystic fibrosis, and so forth.

A reference which relates to inhibition of fructose 1,6-bisphosphatase and reduction of excessive endogenous glucose production and attenuates hyperglycemia is Zucker diabetic fatty rats. van Poelje, Paul D.; Potter, Scott C;. Chandramouli, Visvanathan C.; Landau, Bernard R.; Dang, Qun; Erion, Mark D. Departments of Biochemistry and Medicinal Chemistry, Metabasis Therapeutics, La Jolla, Calif., USA. Diabetes (2006), 55(6), 1747-1754. Publisher: American Diabetes Association.

A reference which relates to fructose 1,6-bisphosphatase inhibitors as preventives for the onset of diabetes is Yoshida, Taishi; Okuno, Akira. (Sankyo Company, Limited, Japan). PCT Int. Appl. (2004), 50 pp. WO 2004009118 A1 20040129

Another reference relating to bisamidate phosphonate prodrugs of FBPase inhibitors for use as antidiabetics is Jaing, Tao; Kasibhatla, Srinivas Rao; Reddy, Raja K. (Metabasis Therapeutics, Inc., USA). PCT Int. Appl. (2001) WO 2001047935.

There is a need, therefore, for novel FBPase inhibitors for the treatment of diseases and disorders.

SUMMARY OF THE INVENTION

In an embodiment of the present invention, provided is a compound of formula (I):

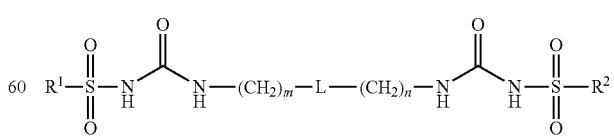

wherein
L is —CH$_2$—, —CH=CH—, —C≡C—, —O—, —S—, —S—S—, cycloalkylene or phenylene, which phenylene can optionally be substituted with halogen;

$R^1$ and $R^2$, independently from each other, are
  a) phenyl which is substituted with a substituent in meta position with regard to the $SO_2$ moiety and optionally with 1 to 2 additional substituents, which substituents are independently selected from the group consisting of halogen, lower-alkyl, cycloalkyl, hydroxy, lower-alkoxy, thio-lower-alkoxy, lower-alkoxy-carbonyl, amido, amino, nitro, cyano, hydroxy-lower-alkyl, halo-lower-alkyl, lower-alkoxy-lower-alkyl, lower-alkyl-C(O)O, heterocyclyl, heterocyclyl-lower-alkyl, aryl, aryl-lower-alkyl, aryloxy and halo-lower-alkoxy, or two substituents are bound together to form a ring together with the carbon atoms to which they are attached and the two substituents together are —$(CH_2)_{2-4}$—; or
  b) heteroaryl, which heteroaryl is optionally substituted with 1 to 3 substituents independently selected from the group consisting of halogen, lower-alkyl, hydroxy, lower-alkoxy, thio-lower-alkoxy, lower-alkoxy-carbonyl, amido, amino, nitro, cyano, hydroxy-lower-alkyl, halo-lower-alkyl, lower-alkoxy-lower-alkyl, heterocyclyl, heterocyclyl-lower-alkyl, aryl, aryl-lower-alkyl, aryloxy and halo-lower-alkoxy;
m is 2, 3 or 4;
n is 2, 3 or 4; or, if L is cycloalkylene or phenylene, which phenylene can optionally be substituted with halogen, m and n can also be 1;
and pharmaceutically acceptable salts or esters thereof, and wherein the compound is not N,N'-[dithiobis(ethane-2,1-diyl-iminocarbonyl)]bis(3,4-dimethylbenzenesulfonamide).

In another embodiment of the present invention, provided is a process for the preparation of a compound according to formula (I), which process comprises the step of reacting a compound of formula (VI)

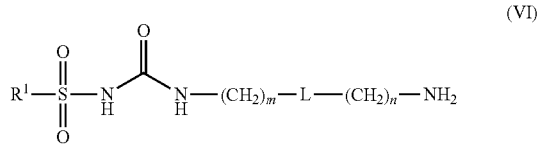

(VI)

with a compound of formula (VIII)

(VIII)

wherein $R^1$, $R^2$, L, m and n are as defined above.

In a further embodiment of the present invention, provided is a pharmaceutical composition, comprising a therapeutically effective amount of a compound according to formula (I) and a therapeutically inert carrier.

In a still another embodiment of the present invention, provided is a method for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, comprising the step of administering a therapeutically effective amount of a compound according to formula (I) to a patient in need thereof.

DETAILED DESCRIPTION

The compounds of formula I and their pharmaceutically acceptable salts and esters are novel and have valuable pharmacological properties. In particular they are FBPase inhibitors and can be used in the prophylaxis and/or treatment of Diabetes Mellitus such as Type I, Type II and Type III Diabetes, Impaired Fasting Glucose (IFG), Impaired Glucose Tolerance (IGT), Metabolic Syndrome, insulin resistance, dyslipidemia, obesity, hypertension, atherosclerosis, diabetic complications, inflammation, respiratory diseases or ischaemia. Preferred is the prophylaxis and/or prevention of progression and/or treatment of Diabetes Mellitus Type II, Diabetes Mellitus Type I, Diabetes Mellitus Type III, Impaired Fasting Glucose (IFG), Impaired Glucose Tolerance (IGT), Metabolic Syndrome, diabetic complications and ischaemia. Particularly preferred is the prophylaxis and/or treatment of Diabetes Mellitus Type II and Diabetes Mellitus Type I. Furthermore, compounds of the present invention can be used in any disease, syndrome, symptom or organ malfunction found associated with increased expression and/or activity of one or another FBPase isoform, at the obvious exception of certain deficiencies where FBPase upregulation might be beneficial for ensuring normal body function, e.g. certain glycogen storage diseases, such as GSD-Type 0 (glycogen synthase deficiency).

Embodiments of the present invention are the compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, particularly Diabetes Mellitus Type II and Diabetes Mellitus Type I.

The compounds of the present invention can be combined with one or more additional active substances indicated for the management of human and veterinary homeostasis in any suitable ratio. Such substances may be insulin sensitizers such as peroxisome proliferator-activated receptor modulators (PPAR alpha, gamma, delta agonists, particularly with thiazolinediones such as rosiglitazone and pioglitazone), insulin secretagogues (sulfonylureas such as glyburide, glimepiride and glipizide, and non-sulfonylurea secretagogues such as the meglitinides repaglinide and nateglinide), insulin, metformin, alpha-glucosidase inhibitors (e.g. acarbose, miglitol), glucagon-like peptide (GLP-1) analogues (e.g. exenatide), dipeptidyl peptidase-IV (DPP-IV) inhibitors, glycogen phosphorylase inhibitors, glycogen synthase kinase-3 inhibitors, 11□-hydroxysteroid dehydrogenase-1 inhibitors, carnitine palmitoyltranferase-1 inhibitors, glucocorticoid receptor antagonists, glucagon receptor antagonists, Adenosine ($A_{2B}$) receptor agonists, amylin agonists (e.g. pramlintide), lipase inhibitor (e.g. orlistat), or any other synthetic or natural substance presenting valuable pharmacological properties useful for the treatment and/or the prevention of metabolic dysfunctions.

In the present description the term "alkyl" or "lower-alkyl", alone or in combination, signifies a straight-chain, branched-chain alkyl group with 1 to 8 carbon atoms, preferably a straight-chain, branched-chain alkyl group with 1 to 6 carbon atoms and particularly preferred a straight or branched-chain alkyl group with 1 to 4 carbon atoms, Examples of straight-chain and branched $C_1$-$C_8$ alkyl groups are methyl, ethyl, propyl, isopropyl, butyl, isobutyl, tert.- butyl, the isomeric pentyls, the isomeric hexyls, the isomeric heptyls and the isomeric octyls, preferably methyl and ethyl and most preferred methyl.

The term "cycloalkyl", alone or in combination, refers to a cyclic alkyl group with 3 to 8 carbon atoms and preferably a cyclic alkyl group with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl.

The term "alkoxy" or "lower-alkoxy", alone or in combination, signifies a group of the formula lower-alkyl-O in which the term "lower-alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "thio-alkoxy" or "thio-lower-alkoxy", alone or in combination, refers to the group alkyl-S— or lower-alkyl-S—, in which the term "alkyl" or "lower-alkyl" has the previously given significance.

The term "halo-lower-alkyl", alone or in combination, signifies a lower-alkyl group as previously defined, wherein one to five hydrogen atoms are substituted by halogen, preferably fluoro. Preferred examples are pentafluoroethyl and particularly trifluoromethyl and difluoromethyl.

The term "halo-lower-alkoxy", alone or in combination, signifies a group of the formula halo-lower-alkyl-O— in which the term "halo-lower-alkyl" is defined as before.

The term "hydroxy-lower-alkyl", alone or in combination, signifies a lower-alkyl group as defined before, wherein one or more hydrogen atoms, preferably one hydrogen atom is replaced by a hydroxy group. Examples of hydroxyalkyl are hydroxymethyl and hydroxyethyl.

The term "cycloalkylene", alone or in combination, signifies a cyclic alkylene group having 3 to 8 carbon atoms and preferably 4 to 6 carbon atoms. An example of a cycloalkylene is cyclohexylene.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, trifluoromethoxy, nitro and trifluoromethyl. Preferred examples are phenyl or phenyl substituted with one to three, preferably one or two substituents independently selected from alkyl, halogen and alkoxy.

The term "aryloxy", alone or in combination, signifies a aryl-O— group in which the term "aryl" has the previously given significance.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl, 1,2,3,4-tetrahydroisoquinolyl and quinoxalinyl. Preferred are oxazolyl, thienyl, pyrazolyl, thiazolyl, 1,2,3-thiadiazolyl and pyrrolidinyl, wherein oxazolyl, thienyl, pyrazolyl, thiazolyl, 1,2,3-thiadiazolyl and pyrrolidinyl are optionally substituted with one to three substituents, preferably one or two substituents independently selected from alkyl, halogen and cyclalkyl, particularly cyclohexyl.

The term "heterocyclyl-lower-alkyl", alone or in combination, signifies the heterocyclyl-alkyl group, wherein the terms "heterocyclyl" and "lower-alkyl" are as previously defined.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "amido", alone or in combination, signifies a group —C(O)— amino, wherein the term "amino" is as previously defined.

The term "halogen", alone or in combination, signifies fluorine, chlorine, bromine or iodine and preferably fluorine, chlorine or bromine.

The term "carbonyl", alone or in combination, signifies the —C(O)— group.

The term "aryl-lower-alkyl", alone or in combination, signifies the aryl-alkyl group, wherein the terms "aryl" and "lower-alkyl" are as previously defined. Preferred is benzyl.

The term "oxy", alone or in combination, signifies the —O— group.

The term "hydroxy", alone or in combination signifies the group —OH.

The term "nitro", alone or in combination signifies the —$NO_2$ group.

The term "cyano", alone or in combination signifies the group —CN.

The term "thio", alone or in combination, signifies the —S— group.

The term "heteroaryl", alone or in combination, signifies an aromatic 5- to 10-membered mono- or bicyclic heterocycle, which contains 1 or 2 heteroatoms selected from nitrogen, oxygen and sulfur. Preferred examples of heteroaryl are furanyl, thiophenyl and benzodioxyl. In addition, thiazolyl, thiophenyl, pyridinyl, pyrimidinyl, pyradizinyl, oxazoyl and isoxazoyl are further preferred heteroaryl groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail the present invention is concerned with compounds of formula (I)

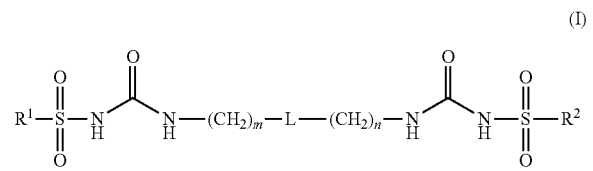

(I)

wherein
L is —CH$_2$—, —CH=CH—, —C≡C—, —O—, —S—, —S—S—, cycloalkylene or phenylene, which phenylene can optionally be substituted with halogen;
R$^1$ and R$^2$, independently from each other, are
a) phenyl which is substituted with a substituent in meta position with regard to the SO$_2$ moiety and optionally with 1 to 2 additional substituents, which substituents are independently selected from the group consisting of halogen, lower-alkyl, cycloalkyl, hydroxy, lower-alkoxy, thio-lower-alkoxy, lower-alkoxy-carbonyl, amido, amino, nitro, cyano, hydroxy-lower-alkyl, halo-lower-alkyl, lower-alkoxy-lower-alkyl, lower-alkyl-C(O)O, heterocyclyl, heterocyclyl-lower-alkyl, aryl, aryl-lower-alkyl, aryloxy and halo-lower-alkoxy, or two substituents are bound together to form a ring together with the carbon atoms to which they are attached and the two substituents together are —(CH$_2$)$_{2-4}$—; or
b) heteroaryl, which heteroaryl is optionally substituted with 1 to 3 substituents independently selected from the group consisting of halogen, lower-alkyl, hydroxy, lower-alkoxy, thio-lower-alkoxy, lower-alkoxy-carbonyl, amido, amino, nitro, cyano, hydroxy-lower-alkyl, halo-lower-alkyl, lower-alkoxy-lower-alkyl, heterocyclyl, heterocyclyl-lower-alkyl, aryl, aryl-lower-alkyl, aryloxy and halo-lower-alkoxy;
m is 2, 3 or 4;
n is 2, 3 or 4; or, if L is cycloalkylene or phenylene, which phenylene can optionally be substituted with halogen, m and n can also be 1;
and pharmaceutically acceptable salts or esters thereof, and wherein the compound is not N,N'-[dithiobis(ethane-2,1-diyl-iminocarbonyl)]bis(3,4-dimethylbenzenesulfonamide).

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Preferred compounds of formula (I) as defined above are those, wherein
L is —CH$_2$—, —CH=CH—, —C≡C—, —O—, —S—, —S—S— or cycloalkylene;
R$^1$ and R$^2$, independently from each other, are
a) phenyl which is substituted with a substituent in meta position with regard to the SO$_2$ moiety and optionally with 1 to 2 additional substituents, which substituents are independently selected from the group consisting of halogen, lower-alkyl, hydroxy, lower-alkoxy, thio-lower-alkoxy, lower-alkoxy-carbonyl, amido, amino, nitro, cyano, hydroxy-lower-alkyl, halo-lower-alkyl, heterocyclyl, heterocyclyl-lower-alkyl, aryl, aryl-lower-alkyl, aryloxy and halo-lower-alkoxy; or
b) heteroaryl, which heteroaryl is optionally substituted with 1 to 3 substituents independently selected from the group consisting of halogen, lower-alkyl, hydroxy, lower-alkoxy, thio-lower-alkoxy, lower-alkoxy-carbonyl, amido, amino, nitro, cyano, hydroxy-lower-alkyl, halo-lower-alkyl, heterocyclyl, heterocyclyl-lower-alkyl, aryl, aryl-lower-alkyl, aryloxy and halo-lower-alkoxy;
m is 2, 3 or 4;
n is 2, 3 or 4; or, if L is cycloalkylene, m and n can also be 1.

Preferred compounds of formula (I) as described above are those, wherein L is —CH$_2$—, —CH=CH—, —O—, —S—, —S—S— or cycloalkylene. More preferably, L is —CH$_2$— or —S—. The different specific moieties, which are possible for L, also individually constitute preferred embodiments.

Other preferred compounds of the present invention are those, wherein R$^1$ and R$^2$, independently from each other, are
a) phenyl which is substituted with a substituent in meta position with regard to the SO$_2$ moiety and optionally with 1 to 2 additional substituents, which substituents are independently selected from the group consisting of halogen, lower-alkyl, hydroxy, lower-alkoxy, amido, amino and nitro; or
b) heteroaryl selected from the group consisting of thiophenyl, furanyl and benzodioxyl, which heteroaryl is optionally substituted with 1 to 3 substituents independently selected from the group consisting of halogen, lower-alkyl, lower-alkoxy-carbonyl, cyano and hydroxy-lower-alkyl.

More preferably, R$^1$ and R$^2$, independently from each other, are phenyl which is substituted with a substituent in meta position with regard to the SO$_2$ moiety with a substituent selected from the group consisting of halogen, lower-alkyl and hydroxy. Even more preferably, R$^1$ and R$^2$ are equal and are 3-chloro-phenyl, 3-methyl-phenyl, 3-fluoro-phenyl or 3-hydroxy-phenyl.

Other preferred compounds of formula (I) as described above are those, wherein R$^1$ and R$^2$, independently from each other, are thiophenyl which is optionally substituted with lower-alkyl. More preferably, $R^1$ and $R^2$ both are 5-methyl-thiophene.

If $R^1=R^2$, symmetrical compounds are obtained which are a preferred embodiment. However, often also unsymmetrical compounds with $R^1 \neq R^2$ are preferred according to the present invention.

Furthermore, it is preferred that m is 2 or 3. It is also preferred that n is 2 or 3. Compounds, wherein m and n are 1, and L is cyclohexylene, are also preferred.

Especially preferred are compounds, wherein the group $—(CH_2)_m$-L-$(CH_2)_n—$ represents a group $—(CH_2)_6—$, $—(CH_2)_7—$, $(CH_2)_5—$ or $—(CH_2)_2—S—(CH_2)_2—$, most preferably $—(CH_2)_6—$ or $—(CH_2)_7—$.

When $R^1$ or $R^2$ are phenyl, they are substituted according to the invention with a substituent in meta position with regard to the $SO_2$ moiety. Especially preferably, such phenyl residue has no further substituent besides the substituent in meta position. In other embodiments, the phenyl residue optionally can be substituted with one to two additional substituents. Both the substituent in meta position and the optional one or two additional substituents are independently selected from the group consisting of halogen, lower-alkyl, hydroxy, lower-alkoxy, thio-lower-alkoxy, lower-alkoxy-carbonyl, amido, amino, nitro, cyano, hydroxy-lower-alkyl, halo-lower-alkyl, heterocyclyl, heterocyclyl-lower-alkyl, aryl, aryl-lower-alkyl, aryloxy and halo-lower-alkoxy. Additional compounds are preferred in which two substituents on the phenyl group form a cyclic moiety together with the two carbon atoms at the phenyl residue, to which they are bound.

More preferred are compounds, in which the one or more substituents at the phenyl residue are selected from Cl, F, Br, methyl, ethyl, $NH_2$, $NO_2$, OH, $—CO—NH_2$, CN or $—O—CH_3$, or wherein two substituents together form a moiety $—O—C(CH_3)_2—O—$ or $—O—CH_2—O—$.

In a further preferred embodiment, $R^1$ and $R^2$ independently from each other are heteroaryl, in particular, heteroaryl having one heteroatom, in particular, one O or one S atom. The heteroaryl residue preferably has one substituent. In case one or more substituents are present, these are preferably selected from halogen, lower-alkyl, lower-alkoxy carbonyl and hydroxy-lower-alkyl, in particular, from Br, Cl, methyl, $—C(O)—O—CH_3$ and hydroxyethyl. In a particularly preferred embodiment, the substituents at the heteroaryl residue are lower-alkyl, in particular, methyl, or the heteroaryl does not have a substituent.

Other preferred compounds as defined above are those, wherein $R^1$ and $R^2$, independently from each other, are
a) phenyl which is substituted with a substituent in meta position with regard to the $SO_2$ moiety and optionally with 1 to 2 additional substituents, which substituents are independently selected from the group consisting of halogen, lower-alkyl, cycloalkyl, hydroxy, halo-lower-alkyl, lower-alkoxy-lower-alkyl, lower-alkyl-C(O)O, or two substituents are bound together to form a ring together with the carbon atoms to which they are attached and the two substituents together are $—(CH_2)_3—$; or
b) heteroaryl, which heteroaryl is optionally substituted with 1 to 3 substituents independently selected from the group consisting of halogen, lower-alkyl and lower-alkoxy-lower-alkyl.

Preferably $R^1$ and $R^2$, independently from each other, are phenyl which is substituted with a substituent in meta position with regard to the $SO_2$ moiety with a substituent selected from the group consisting of hydroxy and lower-alkyl-C(O)O. More preferably, $R^1$ and $R^2$ are equal and are 3-hydroxy-phenyl or 3-acetyl-phenyl.

Other preferred compounds are those, wherein $R^1$ and $R^2$, independently from each other, are thiophenyl which is optionally substituted with 1 to 2 substituents independently selected from lower-alkyl and lower-alkoxy-lower-alkyl. More preferably, $R^1$ and $R^2$ are equal and are 4-methyl-thiophene-2-yl, 5-methyl-thiophene-3-yl, 5-methyl-thiophene-2-yl or 5(2-methoxyethyl)-4-methyl-thiophene-2-yl.

Examples of preferred compounds of formula (I) are those selected from the group consisting of N,N'-[hexane-1,6-diylbis(iminocarbonyl)]bis(3-chlorobenzenesulfonamide), N,N'-[heptane-1,7-diylbis(iminocarbonyl)]bis(3-chlorobenzene-sulfonamide), N,N'-[dithiobis(ethane-2,1-diyliminocarbonyl)]bis(3-chlorobenzenesulfonamide), N,N'-[octane-1,8-diylbis(iminocarbonyl)]bis(3-chlorobenzenesulfonamide), N,N'-[oxybis(propane-3,1-diyliminocarbonyl)]bis(3-chlorobenzenesulfonamide), N,N'-[pentane-1,5-diylbis(iminocarbonyl)]bis(3-chlorobenzenesulfonamide), N,N'-[cyclohexane-1,4-diylbis(methyleneiminocarbonyl)] bis(3-chlorobenzenesulfonamide) cis/trans mixture, N,N'-[hexane-1,6-diylbis(iminocarbonyl)]bis(3-methylbenzenesulfonamide), N,N'-[(3E)-hex-3-ene-1,6-diylbis(iminocarbonyl)]bis(3-chlorobenzenesulfonamide), N,N'-[hexane-1,6-diylbis(iminocarbonyl)]bis(3-fluorobenzenesulfonamide), N,N'-[hexane-1,6-diylbis(iminocarbonyl)]bis(3-aminobenzenesulfonamide), N,N'-[hexane-1,6-diylbis(iminocarbonyl)]bis(3-nitrobenzenesulfonamide), N,N'-[hexane-1,6-diylbis(iminocarbonyl)]bis(5-bromothiophene-2-sulfonamide), N,N'-[hexane-1,6-diylbis(iminocarbonyl)]bis(5-chlorothiophene-2-sulfonamide), N,N'-[thiobis(ethane-2,1-diyliminocarbonyl)]bis(3-methylbenzenesulfonamide), N,N'-[dithiobis(ethane-2,1-diyliminocarbonyl)]bis(3-methylbenzenesulfonamide), N,N'-[hexane-1,6-diylbis(iminocarbonyl)]dithiophene-2-sulfonamide, N,N'-[pentane-1,5-diylbis(iminocarbonyl)]bis(3-methylbenzenesulfonamide), N,N'-[heptane-1,7-diylbis(iminocarbonyl)]bis(3-methylbenzenesulfonamide), N,N'-[octane-1,8-diylbis(iminocarbonyl)]bis(3-methylbenzenesulfonamide), N,N'-[hexane-1,6-diylbis(iminocarbonyl)]bis(5-methylthiophene-2-sulfonamide), dimethyl 5,5'-[hexane-1,6-diylbis(iminocarbonyliminosulfonyl)]dithiophene-2-carboxylate, N,N'-[hexane-1,6-diylbis(iminocarbonyl)]bis(3-bromobenzenesulfonamide), N,N'-[hexane-1,6-diylbis(iminocarbonyl)]bis(3-hydroxybenzene-sulfonamide), N,N'-[hexane-1,6-diylbis(iminocarbonyl)]bis[5-hydroxymethyl)thiophene-2-sulfonamide, N,N-[hexane-1,6-diylbis(iminocarbonyl)]bis(5-bromofuran-2-sulfonamide), N,N'-[hexane-1,6-diylbis(iminocarbonyl)]bis(5-methylfuran-2-sulfonamide), dimethyl 5,5'-[hexane-1,6-diylbis (iminocarbonyliminosulfonyl)]di(2-furoate), 3,3'-[hexane-1,6-diylbis(iminocarbonyliminosulfonyl)] dibenzamide, N,N'-[hexane-1,6-diylbis(iminocarbonyl)]bis(5-cyanothiophene-2-sulfonamide,
N,N'-[hexane-1,6-diylbis(iminocarbonyl)]bis(3-methoxybenzenesulfonamide),
N,N'-[hexane-1,6-diylbis(iminocarbonyl)]bis(3-ethylbenzenesulfonamide),
N,N'-[hexane-1,6-diylbis(iminocarbonyl)]bis(2,2-dimethyl-1,3-benzodioxole-5-sulfonamide),
N,N'-[hexane-1,6-diylbis(iminocarbonyl)]bis(1,3-benzodioxole-5-sulfonamide),
N,N'-[hexane-1,6-diylbis(iminocarbonyl)]bis[5-(hydroxymethyl)furan-2-sulfonamide],
N,N'-[hexane-1,6-diylbis(iminocarbonyl)]bis(3,4-dimethoxybenzenesulfonamide),
N,N'-[hexane-1,6-diylbis(iminocarbonyl)]bis(3-fluoro-4-methylbenzenesulfonamide),
N,N'-[hexane-1,6-diylbis(iminocarbonyl)]bis(3-chloro-4-methylbenzenesulfonamide),
N,N'-[hexane-1,6-diylbis(iminocarbonyl)]bis(3,5-dimethylbenzenesulfonamide), and
N,N'-[hexane-1,6-diylbis(iminocarbonyl)]bis(3,4-dihydroxybenzenesulfonamide),
and pharmaceutically acceptable salts or esters thereof.

Examples of particularly preferred compounds of formula (I) are those selected from the group consisting of
N,N'-[hexane-1,6-diylbis(iminocarbonyl)]bis(3-chlorobenzene-sulfonamide),
N,N'-[heptane-1,7-diylbis(iminocarbonyl)]bis(3-chlorobenzene-sulfonamide),
N,N'-[hexane-1,6-diylbis(iminocarbonyl)]bis(3-methylbenzenesulfonamide),
N,N'-[hexane-1,6-diylbis(iminocarbonyl)]bis(3-fluorobenzenesulfonamide),
N,N'-[thiobis(ethane-2,1-diyliminocarbonyl)]bis(3-methylbenzenesulfonamide),
N,N'-[pentane-1,5-diylbis(iminocarbonyl)]bis(3-methylbenzenesulfonamide),
N,N'-[heptane-1,7-diylbis(iminocarbonyl)]bis(3-methylbenzenesulfonamide),
N,N'-[hexane-1,6-diylbis(iminocarbonyl)]bis(5-methylthiophene-2-sulfonamide), and
N,N'-[hexane-1,6-diylbis(iminocarbonyl)]bis(3-hydroxybenzenesulfonamide),
and pharmaceutically acceptable salts or esters thereof.

Other examples of preferred compounds of formula (I) are those selected from the group consisting of
N,N'-[hexane-1,6-diylbis(iminocarbonyl)]bis(3-cyclopropylbenzenesulfonamide),
N,N'-[hexane-1,6-diylbis(iminocarbonyl)]bis[5-(2-methoxyethyl)-4-methylthiophene-2-sulfonamide],
N,N'-[hexane-1,6-diylbis(iminocarbonyl)]bis(4-methylthiophene-2-sulfonamide),
N,N'-[1,4-phenylenebis(methyleneiminocarbonyl)]bis(3-chlorobenzenesulfonamide),
N,N'-[hexane-1,6-diylbis(iminocarbonyl)]bis(5-methylthiophene-3-sulfonamide),
N,N'-[hexane-1,6-diylbis(iminocarbonyl)]bis(4-bromothiophene-2-sulfonamide),
N,N'-[1,4-phenylenebis(methyleneiminocarbonyl)]bis(3-methylbenzenesulfonamide),
N,N'-[hexane-1,6-diylbis(iminocarbonyl)]diindane-5-sulfonamide,
N,N'-[1,4-phenylenebis(methyleneiminocarbonyl)]bis(3-chloro-4-fluorobenzenesulfonamide),
N,N'-[hexane-1,6-diylbis(iminocarbonyl)]bis[3-(methoxymethyl)benzenesulfonamide],
N,N'-[hexane-1,6-diylbis(iminocarbonyl)]bis[5-(methoxymethyl)thiophene-3-sulfonamide],
3-methyl-N-({6-[({[3-(trifluoromethyl)phenyl]sulfonyl}carbamoyl)amino]hexyl}carbamoyl)benzenesulfonamide,
N,N'-[1,3-phenylenebis(methyleneiminocarbonyl)]bis(3-methylbenzenesulfonamide),
N,N'-[1,4-phenylenebis(methyleneiminocarbonyl)]bis(4-fluoro-3-methylbenzenesulfonamide),
N,N'-[1,4-phenylenebis(methyleneiminocarbonyl)]bis[4-fluoro-3-(trifluoromethyl)benzenesulfonamide],
hexane-1,6-diylbis(iminocarbonyliminosulfonyl-3,1-phenylene)diacetate,
N,N'-[hex-3-yne-1,6-diylbis(iminocarbonyl)]bis(3-methylbenzenesulfonamide),
N,N'-[(2-chloro-1,4-phenylene)bis(methyleneiminocarbonyl)]bis(3-methylbenzenesulfonamide),
N,N'-[hexane-1,6-diylbis(iminocarbonyl)]bis[5-(methoxymethyl)furan-3-sulfonamide],
N,N'-[(2-fluoro-1,4-phenylene)bis(methyleneiminocarbonyl)]bis(3-methylbenzenesulfonamide),
N,N'-[heptane-1,7-diylbis(iminocarbonyl)]bis(5-methylthiophene-3-sulfonamide),
N,N'-[heptane-1,7-diylbis(iminocarbonyl)]bis[5-(methoxymethyl)thiophene-3-sulfonamide],
N,N'-[heptane-1,7-diylbis(iminocarbonyl)]bis[5-(methoxymethyl)furan-3-sulfonamide],
N,N'-[heptane-1,7-diylbis(iminocarbonyl)]bis(3-hydroxybenzenesulfonamide),
N,N'-[(3E)-hex-3-ene-1,6-diylbis(iminocarbonyl)]bis(3-methylbenzenesulfonamide),
N,N'-[(3E)-hex-3-ene-1,6-diylbis(iminocarbonyl)]bis(3-methylbenzenesulfonamide),
N,N'-[heptane-1,7-diylbis(iminocarbonyl)]bis(5-methylthiophene-2-sulfonamide), and heptane-1,7-diylbis(iminocarbonyliminosulfonyl-3,1-phenylene)diacetate,
and pharmaceutically acceptable salts or esters thereof.

Other examples of particularly preferred compounds of formula (I) are those selected from the group consisting of
N,N'-[hexane-1,6-diylbis(iminocarbonyl)]bis[5-(2-methoxyethyl)-4-methylthiophene-2-sulfonamide],
N,N'-[heptane-1,7-diylbis(iminocarbonyl)]bis(5-methylthiophene-3-sulfonamide),
N,N'-[heptane-1,7-diylbis(iminocarbonyl)]bis(3-hydroxybenzenesulfonamide),
N,N'-[(3E)-hex-3-ene-1,6-diylbis(iminocarbonyl)]bis(3-methylbenzenesulfonamide),
N,N'-[heptane-1,7-diylbis(iminocarbonyl)]bis(5-methylthiophene-2-sulfonamide), and heptane-1,7-diylbis(iminocarbonyliminosulfonyl-3,1-phenylene)diacetate,
and pharmaceutically acceptable salts or esters thereof.

In another embodiment, the present invention refers to a process for the preparation of a compound of formula (I) as defined above, which process comprises reacting a compound of formula (VI)

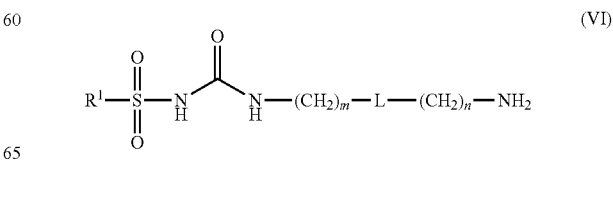

with a compound of formula (VIII)

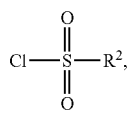
(VIII)

wherein R¹, R², L, m and n are as defined above.

The reaction is preferably carried out in the presence of a salt of hydrocyanic acid, preferably a metal cyanate, more preferably an alkaline metal or alkaline earth metal cyanate, more preferably an alkaline metal cyanate, more preferably sodium cyanate. Preferably, the cyanate and the compound of formula (VIII) form a complex together with a tert. amine such as pyridine. The transformation of a compound of formula (VI) to a compound of formula (I) can conveniently be carried out by methods well known to a person skilled in the art, e.g. by reaction with a complex derived from a compound of the general formula (VIII) with a metal cyanate such as sodium cyanate in the presence of a tert. amine base such as pyridine in an inert solvent such as acetonitrile at temperatures ranging from –78° C. to 100° C. preferably at –10° C. to 40° C. most preferably at room temperature.

Another embodiment of the present invention is related to compounds as defined above, when manufactured according to the process as defined above.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

Compounds of formula I can be prepared as shown in Schemes 1-3 and in the preparative examples 1-69. The starting materials are known compounds or may be prepared by methods well known in the art. In the schemes below, the moiety —(CH₂)ₘ-L-(CH₂)ₙ— is represented as X.

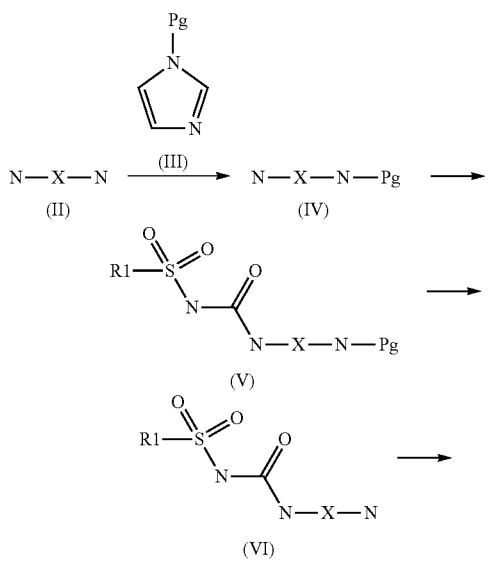

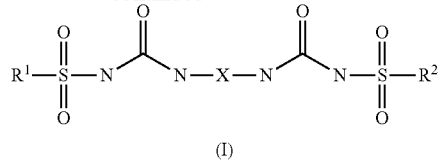
(I)

A symmetrical diamine of the general formula (II) can be transformed into a mono protected diamine of the general formula (IV) in which the group Pg stands for a protective group exemplified by an alkyloxycarbonyl group such as a tert.butyloxycarbonyl, allyloxycarbonyl or benzyloxycarbonyl, by reaction with an intermediates of the general formula (III) which can be derived in situ from commercially available di-alkyl dicarbonates such as di-tert. butyldicarbonate or by the reaction of esters of chloroformic acid such as allylchloroformate or benzylchloroformate with appropriate amounts of imidazol in a suitable inert solvent such as ethers, preferably diethyl ether and tetrahydrofuran, esters preferable ethyl acetate, aromatics, preferably toluene, alkanes, preferable hexane and heptane and halogenated alkanes, preferable dichloromethane and chloroform.

Compounds of the general formula (IV) can be transformed to compounds of the general formula (V) by methods known to the ones skilled in the art, for instance by reaction with a complex derived from a sulfonyl chloride such as m-tolylsulfonylchloride, a metal cyanate such as sodium cyanate and a tert. amine base such as pyridine in an inert solvent such as acetonitrile. The compounds of the general formula (V) can be deprotected by standard methods such as treatment with appropriate acids e.g. formic acid and trifluoroacetic acid for instance in the case of the tert-butyloxycarbonyl protective group or by hydrogenolysis for instance in the case of benzyloxycarbonyl protective group or by palladium (0) catalysed transfer of the allyl group to suitable allyl acceptors such as barbituric acid, dimedon or tri-n-butyltinhydride to yield compounds of the general formula (VI). By applying the methods mentioned above for the transformation of compounds of the general formula (IV) to compounds of the general formula (V) the compounds of the general formula (I) can be obtained from compounds of the general formula (VI). The compounds of the general formula (I) can be dissolved in water at a suitable pH typically 7.00 to 10.00 and purified by reverse phase chromatography. The compounds of the general formula (I) can be transformed to their salts by dissolving them in water by addition of equivalent amounts of suitable bases such as metal hydroxides preferably sodium hydroxide and lyophilisation.

Procedures for the preparation of compounds of the general formula (IA)

Scheme 2

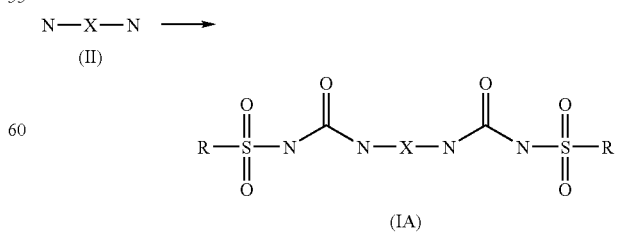

In the special case of R1 and R2 being identical, the corresponding compounds of the general formula (IA) can be obtained from compounds of the general formula (II) by applying the methods mentioned above for the transformation of compounds of the general formula (IV) to compounds of the general formula (V) adjusting the stochiometry to presence of two amino groups in the starting material.

Scheme 3

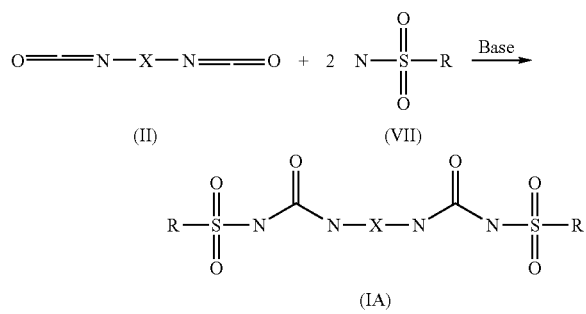

Alternatively compounds of the general formula (IA) can be obtained by reaction of compounds of the general formula (VII) with suitable bases such as metal hydrides, preferably sodium hydride in an inert solvent such as dimethylformamide followed by treatment with a compound of the general formula (II) in a ratio of 2:1. The compounds of the general formula (IA) can be dissolved in water at a suitable pH typically 7.00 to 10.00 and purified by reverse phase chromatography. The compounds of the general formula (IA) can be transformed to their salts by dissolving them in water by addition of equivalent amounts of suitable bases such as metal hydroxides preferably sodium hydroxide and lyophilisation.

The compounds of formula I as described above for use as therapeutically active substance are a further embodiment of the invention.

A further embodiment of the invention are the compounds according to formula I for the preparation of medicaments for the prophylaxis and/or therapy of illnesses which are caused by disorders associated with the enzyme Fructose-1,6-bisphosphatase, preferably Diabetes Mellitus Type II, Diabetes Mellitus Type I, Diabetes Mellitus Type III, Impaired Fasting Glucose (IFG), Impaired Glucose Tolerance (IGT), diabetic complications or ischaemia.

Likewise preferred is a pharmaceutical composition comprising a compound of formula I as described and a therapeutically inert carrier.

A further preferred embodiment of the invention is the use of a compound according to formula I as described for the preparation of medicaments for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia and particularly preferred for the treatment and/or prophylaxis of Diabetes Mellitus Type II or Diabetes Mellitus Type I.

A further embodiment of the present invention is a compound according to formula I, when manufactured according to any one of the described processes.

Likewise preferred is a method for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, which method comprises administering an effective amount of a compound of formula I as described.

Preferred is this method for the treatment and/or prophylaxis of Diabetes Mellitus Type II or Diabetes Mellitus Type I.

Assay Procedures

FBPase Assay Description:

The following tests were carried out for evaluating the inhibitory activity of the compounds of the present invention against human liver FBPase (Swissprot Data base reference PO9467, entry F16P_HUMAN).

Enzyme preparation: Human liver FBPase cDNA (NM_000507) was purchased from Origene Technologies, Inc, subcloned in a vector for expression in *E. Coli.*, and sequenced. Recombinant human liver FBPase (hIFBPase) was purified according to the following protocol that uses heat denaturation similarly to that described by El-Maghrabi et. al. [El-Maghrabi, M. R. et al. "Isolation of a human liver fructose-1,6-bisphosphatase cDNA and expression of the protein in *Escherichia coli.*" J Biol Chem 268:9466-9472, 1993.]. Briefly, *E. coli* cells, transiently expressing very high levels of soluble and active human liver FBPase, were suspended in 20 mM Tris-HCl pH 7.5, 1 mM EDTA, 1 mM DTT and were lysed by French press. The soluble extract was heat denatured at 65° C. for 5 min, and insoluble, denatured proteins were removed by centrifugation. The extract was then applied to a BioRad Macro-Prep High Q column equilibrated with 20 mM Tris-HCl pH 7.5, 1 mM EDTA, 1 mM DTT and the flow-through (containing FBPase activity) was collected and applied to a BioRad Macro-Prep HS column equilibrated with 20 mM HEPES pH 7.2, 1 mM DTT. A gradient of increasing NaCl concentration was then applied to the HS column and fractions were collected. Fractions containing active FBPase were pooled and further purified by size exclusion chromatography on a Sephacryl S200 column equilibrated in 20 mM Tris-HCl pH 7.5, 150 mM NaCl, 1 mM EDTA, 1 mM DTT. Purity of the enzyme preparation was >90% as assessed by Mass spectrometry.

In vitro activity: Recombinant human liver FBPase (hIFBPase) activity was assayed through measuring the inorganic phosphate release that results from the hydrolysis of Fructose-1,6-bisphosphate by the enzyme. As described by Baykov A. A. et al. in [Baykov A. A et al., "Malachite Green procedure for orthophosphate determination and its use in alkaline phosphatase-based enzyme immunoassays". Anal. Biochem., 171:266-270, 1988], inorganic phosphate can be readily quantified by spectrophotometry at 620 nm after complexation with ammonium molybdate/malachite green reagent. Enzymatic reaction was carried out with modifications of the procedure described by Wright S. W. et al. [Wright S. W. et al., "Anilinoquinazoline inhibitors of Fructose-1,6-bisphosphatase bind to a novel allosteric site: synthesis, in vitro characterization, and X-ray crystallography". J. Med. Chem. 45:3865-3877, 2002]. Specifically, the reaction was carried out in 96 well plates in a final volume of 100 μl in the presence or in the absence of allosteric inhibitors. Reaction was started adding 25 ng of hIFBPase to the reaction mixture containing 50 mM HEPES-KOH buffer pH 7.2, 2 mM $MgCl_2$, 2 mM EDTA, 1 mM DTT, 50 μM fructose-1,6-bisphosphate and 1% DMSO. After 50 minutes incubation at room temperature, the phosphate released was allowed to form a colored complex for 10 min by adding 150 μl of ammonium molybdate/malachite green reagent containing 0.03% malachite green, 0.2% ammonium molybdate, 0.05% Triton X-100 and 0.7 M $H_2SO_4$ in water that was stirred for 30 min at room temperature and filtered through 0.2 μm filter. Under these conditions, the assay was linear with time and able to detect FBPase inhibition after spectrophotometric read-out at 620 nm.

Results obtained in the assay above using representative compounds of the invention as the test compounds are shown in the following table:

| Compound | FBPase assay IC$_{50}$ (nM) |
|---|---|
| Example 1 | 17 |
| Example 8 | 22 |

Compounds as described above have IC$_{50}$ values of 1.0 μM to 1 nM; preferred compounds have IC$_{50}$ values of 500 to 1 nM. More preferred compounds have IC$_{50}$ values of 200 to 1 nM. These results have been obtained by using the foregoing test.

In vivo activity. Glucose lowering activity of representative compounds of the present invention was demonstrated after acute treatment in male adult and diabetic db/db mice. db/db mice (12-20 weeks of age) were purchased from Jackson laboratories and time-course effect of compounds on blood glucose levels was measured from tail vein samplings using fluorometric method (Glucotrend systems (Roche AG)).

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), as aerosol formulations or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, the compounds of formula I and their pharmaceutically acceptable salts can be used e.g. for the prophylaxis and/or treatment of diseases which are caused by disorders associated with the enzyme Fructose-1,6-bisphosphatase, particularly of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia. The dosage can vary in wide limits and will, of course, be fitted to the individual requirements in each particular case. In general, in the case of oral administration a daily dosage of about 0.1 mg to 100 mg per kg body weight, preferably about 0.5 mg to 10 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The present invention is therefore also concerned with pharmaceutical compositions comprising a compound as defined above and a therapeutically inert carrier. Furthermore, the present invention is concerned with pharmaceutical compositions comprising a compound as defined above and at least a further active ingredient.

Furthermore, the present invention is concerned with compounds as defined above for use as therapeutically active substance, particularly for the treatment and/or prophylaxis of diseases which are caused by disorders associated with the enzyme Fructose-1,6-bisphosphatase, particularly Diabetes Mellitus Type II, Diabetes Mellitus Type I, Diabetes Mellitus Type III, Impaired Fasting Glucose (IFG), Impaired Glucose Tolerance (IGT), diabetic complications or ischaemia The present invention is also related to the use of compounds as defined above for the preparation of medicaments for the treatment and/or prophylaxis of diseases which are caused by disorders associated with the enzyme Fructose-1, 6-bisphosphatase, particularly Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, more particularly Diabetes Mellitus Type II or Diabetes Mellitus Type I.

In another embodiment, the present invention is concerned with a method for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, which method comprises administering an effective amount of a compound as defined above.

Of the diseases mentioned above, Diabetes Mellitus Type II or Diabetes Mellitus Type I are preferred, particularly Diabetes Mellitus Type II.

The invention is illustrated hereinafter by Examples, which have no limiting character.

EXAMPLES

Example 1

N,N'-[hexane-1,6-diylbis(iminocarbonyl)]bis(3-chlorobenzenesulfonamide

To a solution of 2.53 g chlorobenzenesulfonamide in 20 ml dimethylformamide was added 0.50 g sodium hydride 55% in oil and the mixture was stirred at room temperature for 1.5 hours. To the resulting solution was added a solution of 1.0 g hexamethylenediisocyanate in 10 ml dimethylformamide and the mixture was stirred at room temperature for 20 hours. To the resulting solution was added 1.0 ml methanol. The solvents were removed by distillation under high vacuum. The residue was dissolved in 100 ml water and extracted with 50 ml ethyl acetate (twice). The pH of the aqueous phase was acidified from ca 9 to 1.2 by addition of 1N hydrochloric acid. The solid was collected by filtration washed with water recrystallized from methanol and dried to constant weight under high vacuum to yield 2.57 g of the title compound as white crystals melting at 193-195° C.

Example 2

N,N'-[heptane-1,7-diylbis(iminocarbonyl)]bis(3-chlorobenzenesulfonamide)

To a suspension of 1.00 sodium cyanate in 20 ml acetonitrile was added 0.80 g pyridine and 2.11 g m-chlorophenylsulfonylchloride and the mixture was sonicated in an ultrasound bath at ca 40° C. for 3 h. The solids were removed by filtration. The resulting slightly yellow-orange clear mother liquor was added with stirring to a solution of 0.65 g heptamethylenediamine in 20 ml acetonitrile and the mixture was stirred at room temperature for 1 h.

The product was collected by filtration and recrystallized from methanol to yield the title compound as white crystals melting at 157-165° C.

Example 3

N,N'-[dithiobis(ethane-2,1-diyliminocarbonyl)]bis(3-chlorobenzenesulfonamide)

In analogy to the procedure described in example 2 by substituting heptamethylenediamine with cystamin the title compound was obtained as white crystals melting at 165-167° C. MS (ISN) M−H$^+$=587.2; 585.2

Example 4

N,N'-[octane-1,8-diylbis(iminocarbonyl)]bis(3-chlorobenzenesulfonamide)

In analogy to the procedure described in example 2 by substituting heptamethylenediamine with octamethylenediamine the title compound was obtained as white crystals melting at 178-181° C.

Example 5

N,N'-[oxybis(propane-3,1-diyliminocarbonyl)]bis(3-chlorobenzenesulfonamide)

In analogy to the procedure described in example 2 by substituting heptamethylenediamine with bis(3-aminopropyl)ether the title compound was obtained as white foam. MS (ISN) M−H$^+$=565.1 (100%); 567.1 (99%)

Example 6

N,N'-[pentane-1,5-diylbis(iminocarbonyl)]bis(3-chlorobenzenesulfonamide)

In analogy to the procedure described in example 2 by substituting heptamethylenediamine with pentamethylenediamine the title compound was obtained as white crystals. MS: (ISP) M+H$^+$=537.3 (26%); 539.1 (16%)

Example 7

N,N'-[cyclohexane-1,4-diylbis(methyleneiminocarbonyl)]bis(3-chlorobenzenesulfonamide) cis/trans mixture In analogy to the procedure described in example 2 by substituting heptamethylenediamine with 1,4-cyclohexanebis(methylamine) the title compound was obtained as white foam. MS (ISN) M−H$^+$=575.4 (25%); 577.4 (46%)

Example 8

N,N'-[hexane-1,6-diylbis(iminocarbonyl)]bis(3-methylbenzenesulfonamide)

In analogy to the procedure described in example 1 by substituting m-chlorophenylsulfonamide with m-tolylsulfonamide the title compound was obtained as white crystals melting at 219-220° C.

Example 9

N,N'-[(3E)-hex-3-ene-1,6-diylbis(iminocarbonyl)]bis(3-chlorobenzenesulfonamide)

In analogy to the procedure described in example 2 by substituting heptamethylenediamine with trans-3-hexene-1,6-diamine the title compound was obtained as white solid. MS (ISN) M−H$^+$=547.1 (100%); 549.1 (78%)

Example 10

N,N'-[hexane-1,6-diylbis(iminocarbonyl)]bis(3-fluorobenzenesulfonamide)

In analogy to the procedure described in example 1 by substituting m-chlorophenylsulfonylchloride with m-fluorophenylsulfonylchloride the title compound was obtained as white crystals melting at 199-200° C.

Example 11

N,N'-[hexane-1,6-diylbis(iminocarbonyl)]bis(3-aminobenzenesulfonamide)

In analogy to the procedure described in example 1 by substituting m-chlorophenylsulfonamide with 3-aminobenzenesulfonamide the title compound was obtained as white crystals melting at 178-180° C.

Example 12

N,N'-[hexane-1,6-diylbis(iminocarbonyl)]bis(3-nitrobenzenesulfonamide)

In analogy to the procedure described in example 1 by substituting m-chlorophenylsulfonamide with 3-nitrobenzenesulfonamide the title compound was obtained as white crystals melting at 201-202° C.

Example 13

N,N'-[hexane-1,6-diylbis(iminocarbonyl)]bis(5-bromothiophene-2-sulfonamide)

In analogy to the procedure described in example 1 by substituting m-chlorophenylsulfonamide with 5-bromothiophene-2-sulphonamide the title compound was obtained as white crystals melting at 203-204° C.

Example 14

N,N'-[hexane-1,6-diylbis(iminocarbonyl)]bis(5-chlorothiophene-2-sulfonamide)

In analogy to the procedure described in example 1 by substituting m-chlorophenylsulfonamide with 5-chlorothiophene-2-sulphonamide the title compound was obtained as white crystals melting at 189-191° C.

Example 15

N,N'-[thiobis(ethane-2,1-diyliminocarbonyl)]bis(3-methylbenzenesulfonamide)

In analogy to the procedure described in example 2 by substituting heptamethylenediamine with 2,2'thiobis(ethylamine) and m-chlorophenylsulfonylchloride with 3-methyl-benzenesulfonylchloride the title compound was obtained as white crystals melting at 156-159° C.

Example 16

N,N'-[dithiobis(ethane-2,1-diyliminocarbonyl)]bis(3-methylbenzenesulfonamide)

In analogy to the procedure described in example 3 by substituting m-chlorophenylsulfonylchloride with 3-methyl-benzenesulfonylchloride the title compound was obtained as white crystals melting at 172-175° C.

Example 17

N,N'-[hexane-1,6-diylbis(iminocarbonyl)] dithiophene-2-sulfonamide

In analogy to the procedure described in example 1 by substituting m-chlorophenylsulfonamide with thiophene-2-sulphonamide the title compound was obtained as white crystals melting at 201-202° C.

Example 18

N,N'-[pentane-1,5-diylbis(iminocarbonyl)]bis(3-methylbenzenesulfonamide)

In analogy to the procedure described in example 5 by substituting m-chlorophenylsulfonylchloride with 3-methyl-benzenesulfonylchloride the title compound was obtained as white crystals melting at 170-172° C.

Example 19

N,N'-[heptane-1,7-diylbis(iminocarbonyl)]bis(3-methylbenzenesulfonamide)

In analogy to the procedure described in example 8 by substituting m-chlorophenylsulfonylchloride with 3-methyl-benzenesulfonylchloride the title compound was obtained as white crystals melting at 163-165° C.

Example 20

N,N'-[octane-1,8-diylbis(iminocarbonyl)]bis(3-methylbenzenesulfonamide)

In analogy to the procedure described in example 2 by substituting m-chlorophenylsulfonylchloride with 3-methyl-benzenesulfonylchloride the title compound was obtained as white crystals melting at 189-191° C.

Example 21

N,N'-[hexane-1,6-diylbis(iminocarbonyl)]bis(5-methylthiophene-2-sulfonamide)

In analogy to the procedure described in example 1 by substituting m-chlorophenylsulfonamide with 5-methylthiophene-2-sulfonamide the title compound was obtained as white crystals melting at 185-187° C.

Example 22

Dimethyl 5,5'-[hexane-1,6-diylbis(iminocarbonyliminosulfonyl)]dithiophene-2-carboxylate In analogy to the procedure described in example 1 by substituting m-chlorophenylsulfonamide with 5-sulfamoyl-thiophene-2-carboxylic acid methyl ester the title compound was obtained as white crystals melting at 170-172° C.

Example 23

N,N'-[hexane-1,6-diylbis(iminocarbonyl)]bis(3-bromobenzenesulfonamide)

In analogy to the procedure described in example 1 by substituting m-chlorophenylsulfonamide with m-bromophenylsulfonamide the title compound was obtained as white crystals melting at 178-180° C.

Example 24

N,N'-[hexane-1,6-diylbis(iminocarbonyl)]bis(3-hydroxybenzenesulfonamide)

In analogy to the procedure described in example 1 by substituting m-chlorophenylsulfonamide with 3-hydroxybenzenesulfonamide the title compound was obtained as white crystals melting at 101-102° C.

Example 25

N,N'-[hexane-1,6-diylbis(iminocarbonyl)]bis[5-(hydroxymethyl)thiophene-2-sulfonamide]

In analogy to the procedure described in example 1 by substituting m-chlorophenylsulfonamide with 5-hydroxymethyl-thiophene-2-sulfonic acid amide the title compound was obtained as white crystals melting at 128-130° C.

Example 25b 5-hydroxymethyl-thiophene-2-sulfonic acid amide

The starting material 5-hydroxymethyl-thiophene-2-sulfonic acid amide was prepared from 5-sulfamoyl-thiophene-2-carboxylic acid methyl ester as follows.

To a solution of 0.442 g 5-sulfamoyl-thiophene-2-carboxylic acid methyl ester in 8 ml tetrahydrofuran was added 0.044 g lithiumborohydride and the mixture was stirred at room temperature for 20 h. To the resulting mixture was added another 0.088 g lithiumborohydride and the mixture was stirred at room temperature for 2 h and at reflux for 20 h. The resulting suspension was partitioned between water and ethyl acetate. The phases were separated and the organic phase was purified by chromatography on silica gel with ethyl acetate to yield 0.300 g of the title compound as white crystals melting at 70-71° C.

Example 26

N,N'-[hexane-1,6-diylbis(iminocarbonyl)]bis(5-bromofuran-2-sulfonamide)

In analogy to the procedure described in example 1 by substituting m-chlorophenylsulfonamide with 5-bromofuran-2-sulfonamide the title compound was obtained as white crystals melting at 183-185° C.

The starting material 5-bromofuran-2-sulfonamide was prepared from 2,5-dibromofuran as follows.

To a solution of 8.00 g 2,5-dibromofuran in 80 ml tetrahydrofuran was drop wise added at −78° C. 17.5 ml of a 2M solution of isopropylmagnesium chloride in diethyl ether and the mixture was stirred at −78° C. for 3 h. To the resulting suspension was drop wise added ca 6.0 ml liquid sulfurdioxide (dry ice condenser) whereby a solution resulted. The mixture was stirred at −78° C. for 30 min and at room temperature for 2 h. The formed solid was collected by filtration and dried to constant weight to yield 6.76 g of a white solid.

To a solution of 2.1 g of this solid in 20 ml water was added 0.90 g sodium acetate and 1.24 g hydroxylamine-O-sulfonic acid and the mixture was stirred at room temperature for 18 h. The product was collected by filtration to yield 1.05 g of the title compound as white solid melting at 98-99° C.

Example 27

N,N'-[hexane-1,6-diylbis(iminocarbonyl)]bis(5-methylfuran-2-sulfonamide)

In analogy to the procedure described in example 1 by substituting m-chlorophenylsulfonamide with 5-methylfuran-2-sulfonamide the title compound was obtained as white crystals melting at 170-171° C.

The starting material 5-methylfuran-2-sulfonamide was prepared from 5-bromofuran-2-sulfonamide as follows.

To a solution of 0.452 g 5-bromofuran-2-sulfonamide in 8 ml 1,2-dimethoxyethan was added 0.24 g tetrakistriphenylphosphinpalladium, a solution of 0.536 g sodium carbonate in 3 ml water and a solution of 0.528 g trimethylboroxine in 0.6 ml tetrahydrofuran and 2.0 ml 1,2-dimethoxyethan and the mixture was heated to reflux for 18 h. The dark reaction mixture was partitioned between water and ethyl acetate. The phases were separated and the organic phase was purified by chromatography on silica gel with heptane:ethyl acetate=2:1 to yield 0.239 g of the title compound as white crystals melting at 115-116° C.

Example 28

Dimethyl 5,5'-[hexane-1,6-diylbis(iminocarbonyliminosulfonyl)]di(2-furoate)

In analogy to the procedure described in example 1 by substituting m-chlorophenylsulfonamide with 2-furancarboxylic acid, 5-(aminosulfonyl)-, methyl ester the title compound was obtained as white crystals melting at 203-204° C.

Example 29

3,3'-[Hexane-1,6-diylbis(iminocarbonyliminosulfonyl)]dibenzamide

In analogy to the procedure described in example 1 by substituting m-chlorophenylsulfonamide with 3-sulfamylbenzamide the title compound was obtained as white crystals melting at 192-194° C.

Example 30

N,N'-[hexane-1,6-diylbis(iminocarbonyl)]bis(5-cyanothiophene-2-sulfonamide)

In analogy to the procedure described in example 1 by substituting m-chlorophenylsulfonamide with 5-cyanothiophene-2-sulfonic acid amide the title compound was obtained as white crystals melting at 192-194° C.

Example 31

N,N'-[hexane-1,6-diylbis(iminocarbonyl)]bis(3-methoxybenzenesulfonamide)

In analogy to the procedure described in example 1 by substituting m-chlorophenylsulfonamide with 3-methoxybenzenesulfonamide the title compound was obtained as white crystals melting at 194-196° C.

Example 32

N,N'-[hexane-1,6-diylbis(iminocarbonyl)]bis(3-ethylbenzenesulfonamide)

In analogy to the procedure described in example 1 by substituting m-chlorophenylsulfonamide with 3-ethyl-benzenesulfonamide the title compound was obtained as white crystals melting at 185-186° C.

Example 33

N,N'-[hexane-1,6-diylbis(iminocarbonyl)]bis(2,2-dimethyl-1,3-benzodioxole-5-sulfonamide)

In analogy to the procedure described in example 1 by substituting m-chlorophenylsulfonamide with 2,2-dimethylbenzo[1,3]dioxole-5-sulfonic acid amide the title compound was obtained as white crystals melting at 210-212° C.

Example 34

N,N'-[hexane-1,6-diylbis(iminocarbonyl)]bis(1,3-benzodioxole-5-sulfonamide)

In analogy to the procedure described in example 1 by substituting m-chlorophenylsulfonamide with benzo[1,3]dioxole-5-sulfonic acid amide the title compound was obtained as white crystals melting at 197-199° C.

Example 35

N,N'-[hexane-1,6-diylbis(iminocarbonyl)]bis[5-(hydroxymethyl)furan-2-sulfonamide]

In analogy to the procedure described in example 1 by substituting m-chlorophenylsulfonamide with 5-hydroxymethyl-furan-2-sulfonic acid amide the title compound was obtained as white crystals melting at 129-130° C.

The starting material 5-hydroxymethyl-furan-2-sulfonic acid amide was obtained in analogy to example 25b by substituting 5-sulfamoyl-thiophene-2-carboxylic acid methyl ester with 5-sulfamoyl-furan-2-carboxylic acid methyl ester.

Example 36

N,N'-[hexane-1,6-diylbis(iminocarbonyl)]bis(3,4-dimethoxybenzenesulfonamide)

In analogy to the procedure described in example 1 by substituting m-chlorophenylsulfonamide with 3,4-dimethoxybenzenesulfonamide the title compound was obtained as white crystals melting at 211-213° C.

Example 37

N,N'-[hexane-1,6-diylbis(iminocarbonyl)]bis(3-fluoro-4-methylbenzenesulfonamide)

In analogy to the procedure described in example 1 by substituting m-chlorophenylsulfonamide with 3-fluoro-4-methyl-benzenesulfonamide the title compound was obtained as white crystals melting at 185-187° C.

Example 38

N,N'-[hexane-1,6-diylbis(iminocarbonyl)]bis(3-chloro-4-methylbenzenesulfonamide)

In analogy to the procedure described in example 1 by substituting m-chlorophenylsulfonamide with 3-chloro-4-methyl-benzenesulfonamide the title compound was obtained as white crystals melting at 183-185° C.

Example 39

N,N'-[hexane-1,6-diylbis(iminocarbonyl)]bis(3,5-dimethylbenzenesulfonamide)

In analogy to the procedure described in example 1 by substituting m-chlorophenylsulfonamide with 3,5-dimethylbenzenesulfonamide the title compound was obtained as white crystals melting at 215-217° C.

Example 40

N,N'-[hexane-1,6-diylbis(iminocarbonyl)]bis(3,4-dimethylbenzenesulfonamide)

In analogy to the procedure described in example 1 by substituting m-chlorophenylsulfonamide with 3,3-dimethylbenzenesulfonamide the title compound was obtained as white crystals.

Example 41

3-chloro-N-{[6-({[(3-methylphenyl)sulfonyl]carbamoyl}amino)hexyl]carbamoyl}benzenesulfonamide To a suspension of 0.047 sodium cyanate in 2 ml acetonitrile was added 0.042 g pyridine and 0.111 g m-chlorophenylsulfonylchloride and the mixture was agitated in an ultrasound bath under argon for ca 1 h. The suspension was allowed to settle. The clear supernatant was collected with a syringe (1.0 ml) and added to a suspension of 0.05 g of the product of example 41a N-[(6-aminohexyl)carbamoyl]-3-methylbenzenesulfonamide in 2 ml acetonitrile and the mixture was stirred at room temperature for 1 h and kept at room temperature for 18 h. The mixture was evaporated and the residue was dissolved in 1M sodium hydroxide and purified by chromatography on MCI gel with a gradient of 0.1M sodium hydroxide to 0.1M sodium hydroxide: acetonitrile=7:3. The product fractions were collected and concentrated to ca 10 ml. The pH was adjusted to 2.00 by addition of 25% hydrochloric acid. The white precipitate was collected by filtration and dried to constant weight to yield 0.030 g of the title compound as white crystals melting at 187-189° C.

Example 41a

N-[(6-aminohexyl)carbamoyl]-3-methylbenzenesulfonamide

The starting material was prepared as follows.

To a suspension of 0.47 sodium cyanate in 20 ml acetonitrile was added 0.42 g pyridine and 0.95 g m-methylphenylsulfonylchloride and the mixture was agitated in an ultrasound bath under argon for ca 1 h. The resulting suspension was added to a solution of 0.500 g N-mono-tert.butyloxycarbonylhexamethylenediamine in 10 ml acetonitrile and the mixture was stirred at room temperature for 2 h. The solvent was evaporated and the residue was partitioned between dichlormethane and 1N sodium hydroxide. The phases were separated and the aqueous phase was acidified by addition of citric acid and extracted with dichloromethane. The second organic phase was washed with half concentrated brine and purified by chromatography on silica gel with heptane:ethyl acetate=1:1. The product fractions were collected and evaporated. The residue was taken up in 5 ml trifluoro acetic acid and kept at room temperature for 4 h. The solvent was evaporated and the residue was taken up in methanol and purified by chromatography on silica gel with a gradient of dichloromethane:methanol:ammonia=19:1:0.1 to 7:3:0.2. The product fractions were concentrated under aspirator vacuum whereby crystallisation occurred. The product was recrystallized from methanol to yield 0.180 g of the title compound as white crystals melting at 186.7-187.4° C.

Example 42

N,N'-[hexane-1,6-diylbis(iminocarbonyl)]bis(3-cyclopropylbenzenesulfonamide)

In analogy to the procedure described in example 1 by substituting m-chlorophenylsulfonamide with 3-cyclopropylbenzenesulfonamide the title compound was obtained as white crystals melting at 190-192° C.

Example 42a 3-cyclopropylbenzenesulfonamide

To a solution of 0.985 g 1-bromo-3-cyclopropyl-benzene in 5 ml tetrahydrofuran was drop wise added at −78° C. 2.81 ml of a 1.6M solution of n-butyllithium in hexane. The mixture was stirred at −78° C. for 1.5 h. To the resulting suspension was added drop wise an excess (ca 1.5 ml) of sulfur dioxide (condensed with a dry ice cooling trap) and the mixture was allowed to taw to room temperature. The resulting suspension was stirred at room temperature for 45 min. The solid was collected by filtration washed with heptane and dried under high vacuum to constant weight to yield 0.67 g of a light yellow solid. This material was dissolved in 5.0 ml water and 0.467 g sodium acetate and 0.604 g hydroxylamine-O-sulfonic acid was added. The reaction mixture was stirred for 30 min at ambient temperature whereby a precipitate formed. The solid was collected and washed with water and dried to constant weight to yield 0.44 g of the title compound as a light yellow solid melting at 71.5-72.9° C.

Example 43

N,N'-[hexane-1,6-diylbis(iminocarbonyl)]bis[5-(2-methoxyethyl)-4-methylthiophene-2-sulfonamide]

In analogy to the procedure described in example 2 by substituting m-chlorophenylsulfonylchloride with 5-(2-methoxy-ethyl)-4-methyl-thiophene-2-sulfonyl chloride and heptamethylenediamine with hexamethylenediamine the title compound was obtained as white solid. MS (ISN) M−H+= 637.2

Example 43a 2-(2-methoxy-ethyl)-3-methyl-thiophene

A part of a solution containing 2-bromo-3-methylthiophene CAS14282-76-9 (1.5 g, 8.5 mmol) in dry diethyl ether was added drop-wise to a suspension of magnesium (308 mg, 12.7 mmol, 1.5 equiv.) in dry diethyl ether, until the mixture started to reflux. The remaining solution was added dropwise. A solution of toluene-4-sulfonic acid 2-methoxy-ethyl ester (2.9 g, 12.7 mmol, 1.5 equiv.) in dry diethyl ether was added dropwise at room temp., then the mixture was refluxed for two hours. After cooling down to room temp., the mixture was quenched with ammonium chloride solution saturated and extracted with tert. butylmethyl ether. The combined organic extracts were washed with water and brine, dried over magnesiumsulfate-dihydrate and purified on silica gel with eluent n-heptane and tert.butylmethyl ether. The title compound was obtained as light yellow oil: 490 mg, GC-MS (EI) M=156.

Example 43b 5-(2-methoxy-ethyl)-4-methyl-thiophene-2-sulfonyl chloride

Sulfuryl chloride (0.26 g, 1.9 mmol) was added dropwise to a stirred solution of dry DMF (0.14 ml, 1.9 mmol) at 0° C. under an argon atmosphere resulting in the formation of a white solid. After 15 min, 2-(2-methoxy-ethyl)-3-methyl-thiophene (250 mg, 1.6 mmol) was added and the mixture was warmed to 100° C. and the melt was further stirred for 45 min. Crushed ice was added and the reaction mixture was extracted with ethyl acetate (2×) and the combined organic extracts were washed with water, brine, dried (magnesium sulfate. dihydrate), filtered and concentrated under reduced pressure. The crude solid was purified over silica gel (ethyl acetate/n-heptane): light yellow oil, 220 mg, GC-MS (EI): M=254.

Example 44

N,N'-[Hexane-1,6-diylbis(iminocarbonyl)]bis(4-methylthiophene-2-sulfonamide)

In analogy to the procedure described in example 1 by substituting m-chlorophenylsulfonamide with 4-methyl-thiophene-2-sulfonic acid amide the title compound was obtained as white crystals melting at 196-197° C.

Example 45

N,N'-[1,4-phenylenebis(methyleneiminocarbonyl)]bis(3-chlorobenzenesulfonamide)

In analogy to the procedure described in example 2 by substituting heptamethylenediamine with 4-aminomethyl-benzylamine the title compound was obtained as white solid. MS (ISN) M−H+=570.4

Example 46

N,N'-[Hexane-1,6-diylbis(iminocarbonyl)]bis(5-methylthiophene-3-sulfonamide)

In analogy to the procedure described in example 1 by substituting m-chlorophenylsulfonamide with 5-methylthiophene-3-sulfonamide the title compound was obtained as white crystals melting at 169-171° C.

Example 46a

5-Methyl-thiophene-3-sulfonic acid amide

In analogy to example 42a by substituting 1-bromo-3-cyclopropyl-benzene by 4-bromo-2-methyl-thiophene and using t-butyl lithium instead of n-butyl lithium the title compound was obtained as white solid melting at 102-104.3° C.

Example 47

N,N'-[Hexane-1,6-diylbis(iminocarbonyl)]bis(4-bromothiophene-2-sulfonamide)

In analogy to the procedure described in example 1 by substituting m-chlorophenylsulfonamide with 4-bromo-thiophene-2-sulfonic acid amide the title compound was obtained as white crystals melting at 182-183° C.

Example 48

N,N'-[1,4-Phenylenebis(methyleneiminocarbonyl)]bis(3-methylbenzenesulfonamide)

In analogy to the procedure described in example 2 by substituting heptamethylenediamine with 4-aminomethyl-benzylamine and m-chlorophenylsulfonylchloride with 3-methylbenzenesulfonylchloride the title compound was obtained as colorless solid. MS (ISN) M−H+=529.4

Example 49

N,N'-[hexane-1,6-diylbis(iminocarbonyl)]diindane-5-sulfonamide

In analogy to the procedure described in example 1 by substituting m-chlorobenzenesulfonamide with indan-5-sulfonic acid amide the title compound was obtained as white solid melting at 168-169° C.

Example 50

N,N'-[1,4-Phenylenebis(methyleneiminocarbonyl)]bis(3-chloro-4-fluorobenzenesulfonamide)

In analogy to the procedure described in example 2 by substituting heptamethylenediamine with 4-aminomethylbenzylamine and m-chlorophenylsulfonylchloride with 3-chloro-4-fluoro-benzenesulfonylchloride the title compound was obtained as off-white solid. MS (ISN) M−H$^+$=605.4

Example 51

N,N'-[Hexane-1,6-diylbis(iminocarbonyl)]bis[3-(methoxymethyl)benzenesulfonamide]

In analogy to the procedure described in example 1 by substituting m-chlorobenzenesulfonamide with 3-methoxymethyl-benzenesulfonamide the title compound was obtained as white solid melting at 160-162° C.

Example 51a 3-Methoxymethyl-benzenesulfonamide

In analogy to example 42a by substituting 1-bromo-3-cyclopropyl-benzene by 1-bromo-3-methoxymethyl-benzene the title compound was obtained as oil. MS (ISN) M−H$^+$=200.1

Example 52

N,N'-[Hexane-1,6-diylbis(iminocarbonyl)]bis[5-(methoxymethyl)thiophene-3-sulfonamide]

In analogy to the procedure described in example 1 by substituting m-chlorobenzenesulfonamide with 5-methoxymethyl-thiophene-3-sulfonic acid amide the title compound was obtained as white solid melting at 154-156° C.

Example 52a

5-Methoxymethyl-thiophene-3-sulfonic acid amide

In analogy to example 42a by substituting 1-bromo-3-cyclopropyl-benzene by 4-bromo-2-methoxymethyl-thiophene (CAS141832-35-1) and using t-butyl lithium instead of n-butyl lithium the title compound was obtained as white solid melting at 74.2-75.7° C.

Example 53

3-Methyl-N-({6-[({[3-(trifluoromethyl)phenyl]sulfonyl}carbamoyl)amino]hexyl}carbamoyl)benzenesulfonamide In analogy to example 41 by substituting by substituting m-chlorobenzenesulfonamide with 3-trifluoromethyl-benzenesulfonamide the title compound was obtained as white solid. MS (ISN) M−H$^+$=563.2

Example 54

N,N'-[1,3-Phenylenebis(methyleneiminocarbonyl)]bis(3-methylbenzenesulfonamide)

In analogy to the procedure described in example 2 by substituting heptamethylenediamine with 3-aminomethyl-benzylamine and m-chlorophenylsulfonylchloride with 3-methylbenzenesulfonylchloride the title compound was obtained as light-yellow solid. MS (ISN) M−H$^+$=528.9

Example 55

N,N'-[1,4-Phenylenebis(methyleneiminocarbonyl)]bis(4-fluoro-3-methylbenzenesulfonamide)

In analogy to the procedure described in example 2 by substituting heptamethylenediamine with 4-aminomethyl-benzylamine and m-chlorophenylsulfonylchloride with 3-methyl-4-fluoro-benzenesulfonylchloride the title compound was obtained as off-white solid. MS (ISN) M−H$^+$=673.2

Example 56

N,N'-[1,4-Phenylenebis(methyleneiminocarbonyl)]bis[4-fluoro-3-(trifluoromethyl)benzenesulfonamide]

In analogy to the procedure described in example 2 by substituting heptamethylenediamine with 4-aminomethyl-benzylamine and m-chlorophenylsulfonylchloride with 3-trifluoromethyl-4-fluoro-benzenesulfonylchloride the title compound was obtained as light-yellow solid.
MS (ISN) M−H$^+$=673.2

Example 57

Hexane-1,6-diylbis(iminocarbonyliminosulfonyl-3,1-phenylene)diacetate

To a suspension of 0.103 g of N,N'-[hexane-1,6-diylbis(iminocarbonyl)]bis(3-hydroxybenzenesulfonamide) (Example 24) in 5.0 ml acetic acid anhydride was added 0.005 g N',N'dimethylaminopyridine and the mixture was stirred at ambient temperature for 24 h. The resulting solid was collected by filtration and washed with acetic acid anhydride and dried to constant weight to yield the title compound as white crystals melting at 180-182° C.

Example 58

N,N'-[Hex-3-yne-1,6-diylbis(iminocarbonyl)]bis(3-methylbenzenesulfonamide)

In analogy to the procedure described in example 2 by substituting heptamethylenediamine with hex-3-yne-1,6-diamine and m-chlorophenylsulfonylchloride with 3-methyl-benzenesulfonylchloride the title compound was obtained as white solid. MS (ISN) M−H$^+$=505.0

Example 59

N,N'-[(2-chloro-1,4-phenylene)bis(methyleneiminocarbonyl)]bis(3-methylbenzenesulfonamide)

In analogy to the procedure described in example 2 by substituting heptamethylenediamine with 4-aminomethyl-3-chloro-benzylamine and m-chlorophenylsulfonylchloride with 3-methyl-benzenesulfonylchloride the title compound was obtained as white solid. MS (ISN) M−H$^+$=563.1

Example 59a 4-aminomethyl-3-chloro-benzylamine

The starting material 4-aminomethyl-3-chloro-benzylamine was prepared from 1,4-bis-bromomethyl-2-chloro-benzene as follows. A suspension of 1,4-bis-bromomethyl-2-chloro-benzene (470 mg) and sodiumazide (225 mg) in dimethylformamide (2.5 ml) was stirred at 60° C. for 2 hours. The reaction mixture was then diluted with water and extracted with ether. The combined organic extracts were then washed with water, dried (Na2SO4) and evaporated. Part of the remaining residue (233 mg) was dissolved in methanol (5 ml) and tin(II) chloride (962 mg) was added portionwise at 0° C. The reaction mixture was then stirred at room temperature over night. The solvent was removed and the residue was dissolved in 3N sodium hydroxide (12 ml) and this solution was saturated with sodium chloride and extracted with chloroform. The combined extracts were dried (sodium sulfate) and evaporated and the remaining material was purified by chromatography (dichloromethane/methanol/ammonia 19:1: 0.1 and 9:0.9:0.1). 4-Aminomethyl-3-chloro-benzylamine was obtained as light yellow oil (76 mg).

Example 60

N,N'-[Hexane-1,6-diylbis(iminocarbonyl)]bis[5-(methoxymethyl)furan-3-sulfonamide]

In analogy to the procedure described in example 1 by substituting m-chlorobenzenesulfonamide with 5-methoxymethyl-furan-3-sulfonic acid amide the title compound was obtained as white solid melting at 149-150° C.

Example 60a

5-Methoxymethyl-furan-3-sulfonic acid amide

In analogy to example 42a by substituting 1-bromo-3-cyclopropyl-benzene by 4-bromo-2-methoxymethyl-furan and using t-butyl lithium instead of n-butyl lithium the title compound was obtained as white solid melting at 73.2-75.3° C.

Example 60b

4-Bromo-2-methoxymethyl-furan

To a solution of 1.062 g (4-bromo-furan-2-yl)-methanol in 10 ml dimethylsulfoxide was added 0.288 of sodium hydride (55%) in oil and 0.56 ml of iodomethane and the reaction mixtures was stirred at room temperature for 18 h. The reaction mixture was partitioned between ethyl acetate and water. The phases were separated; the organic phase was washed with citric acid (10% in water), water, satd. sodiumbicarbonate and brine, dried over magnesium sulfate and evaporated under reduced pressure. The residue was purified by chromatography on silica gel to yield 0.731 g of a light yellow liquid.

Example 61

N,N'-[(2-fluoro-1,4-phenylene)bis(methyleneiminocarbonyl)]bis(3-methylbenzenesulfonamide)

In analogy to the procedure described in example 2 by substituting heptamethylenediamine with 4-aminomethyl-3-fluoro-benzylamine and m-chlorophenylsulfonylchloride with 3-methyl-benzenesulfonylchloride the title compound was obtained as off-white solid. MS (ISN) M−H$^+$=547.0

Example 61a

4-Aminomethyl-3-fluoro-benzylamine

The starting material 4-aminomethyl-3-fluoro-benzylamine was prepared from 1,4-bis-bromomethyl-2-fluorobenzene as described for 4-aminomethyl-3-chloro-benzylamine in example 59a Example 62

N,N'-[heptane-1,7-diylbis(iminocarbonyl)]bis(5-methylthiophene-3-sulfonamide)

To a solution of 0.35 g 5-methyl-thiophene-3-sulfonic acid amide (example 46a) in 10 ml dimethylformamide was added 0.080 g sodium hydride 55% in oil and the mixture was stirred at room temperature for 30 min. To the resulting solution was added dropwise 0.180 g heptamethylene diisocyanate (CAS18020-78-5) and the mixture was stirred at room temperature for 2 h. The solvent was evaporated and the residue was partitioned between water and ethyl acetate. The phases were separated and the aqueous phase was washed with ethyl acetate and purified by chromatography on 100 ml MCl gel with a gradient (water 0-50% acetonitrile) The product fractions were collected and the product was precipitated by adjusting the pH to 2.00 by addition of 1N hydrochloric acid. The solid was collected by filtration and washed with water and dried to constant weight to yield 0.24 g of the title compound as white powder. MS (ISN) M−H$^+$=536.0

Example 63

N,N'-[heptane-1,7-diylbis(iminocarbonyl)]bis[5-(methoxymethyl)thiophene-3-sulfonamide]

In analogy to the procedure described in example 62 by substituting 5-methyl-thiophene-3-sulfonic acid amide with 5-methoxymethyl-thiophene-3-sulfonic acid amide (example 52a) the title compound was obtained as white solid melting at 130-131° C.

Example 64

N,N'-[heptane-1,7-diylbis(iminocarbonyl)]bis[5-methoxymethyl)furan-3-sulfonamide]

In analogy to the procedure described in example 62 by substituting 5-methyl-thiophene-3-sulfonic acid amide with 5-methoxymethyl-furan-3-sulfonic acid amide (example 60a) the title compound was obtained as white solid melting at 138-139° C.

Example 65

N,N'-[heptane-1,7-diylbis(iminocarbonyl)]bis(3-hydroxybenzenesulfonamide)

In analogy to the procedure described in example 62 by substituting 5-methyl-thiophene-3-sulfonic acid amide with 3-hydroxy-benzenesulfonamide the title compound was obtained as white solid melting at 162-163° C.

Example 66

N,N'-[(3E)-hex-3-ene-1,6-diylbis(iminocarbonyl)]bis(3-methylbenzenesulfonamide)

In analogy to the procedure described in example 9 by substituting m-chlorophenylsulfonamide with m-tolylsulfonamide the title compound was obtained as white solid. MS (ISN) M–H$^+$=507.0

Example 67

N,N'-[(3E)-hex-3-ene-1,6-diylbis(iminocarbonyl)]bis(3-methylbenzenesulfonamide)

In analogy to the procedure described in example 62 by substituting 5-methyl-thiophene-3-sulfonic acid amide with 4-methyl-thiophene-2-sulfonic acid amide the title compound was obtained as white solid melting at 172-173° C.

Example 68

N,N'-[Heptane-1,7-diylbis(iminocarbonyl)]bis(5-methylthiophene-2-sulfonamide)

In analogy to the procedure described in example 62 by substituting 5-methyl-thiophene-3-sulfonic acid amide with 5-methyl-thiophene-2-sulfonic acid amide the title compound was obtained as white solid melting at 192-193° C.

Example 69

Heptane-1,7-diylbis(iminocarbonyliminosulfonyl-3,1-phenylene)diacetate

In analogy to the procedure described in example 57 by substituting N,N'-[hexane-1,6-diylbis(iminocarbonyl)]bis(3-hydroxybenzenesulfonamide) (example 24) by N,N'-[heptane-1,7-diylbis(iminocarbonyl)]bis(3-hydroxybenzenesulfonamide) (example 65) the title compound was obtained as white solid melting at 170-171° C.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

It is to be understood that the invention is not limited to the particular embodiments of the invention described above, as variations of the particular embodiments may be made and still fall within the scope of the appended claims

What is claimed is:
1. A compound of formula (I):

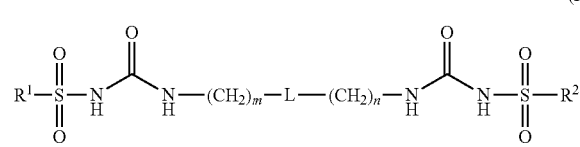

wherein
L is —CH$_2$—, or —S;
R$^1$ and R$^2$, independently from each other, are
  a) phenyl which is substituted with a substituent in meta position with regard to the SO$_2$ moiety optionally with 1 to 2 additional substituents, which substituents are independently selected from the group consisting of halogen, lower-alkyl, hydroxy, lower-alkoxy, amido, amino and nitro; or
  b) heteroaryl selected from the group consisting of thiophenyl, furanyl and benzodioxyl, which heteroaryl is optionally substituted with 1 to 3 substituents independently selected from the group consisting of halogen, lower-alkyl, lower-alkoxy-carbonyl, cyano and hydroxy-lower-alkyl;
m is 2, 3 or 4;
n is 2, 3 or 4;
and pharmaceutically acceptable salts or esters thereof, and wherein the compound is not N,N'-[dithiobis(ethane-2,1-diyl-iminocarbonyl)]bis(3,4-dimethylbenzenesulfonamide).

2. The compound according to claim 1, wherein R$^1$ and R$^2$, independently from each other, are phenyl which is substituted with a substituent in meta position with regard to the SO$_2$ moiety with a substituent selected from the group consisting of halogen, lower-alkyl and hydroxy.

3. The compound according to claim 1, wherein R$^1$ and R$^2$ are equal and are 3-chloro-phenyl, 3-methyl-phenyl, 3-fluoro-phenyl or 3-hydroxy-phenyl.

4. The compound according to claim 1, wherein R$^1$ and R$^2$, independently from each other, are thiophenyl which is optionally substituted with lower-alkyl.

5. The compound according to claim 1, wherein R$^1$ and R$^2$ both are 5-methyl-thiophene.

6. The compound according to claim 1, wherein R$^1$ and R$^2$, independently from each other, are
  a) phenyl which is substituted with a substituent in meta position with regard to the SO$_2$ moiety and optionally with 1 to 2 additional substituents, which substituents are independently selected from the group consisting of halogen, lower-alkyl, cycloalkyl, hydroxy, halo-lower-alkyl, lower-alkoxy-lower-alkyl, lower-alkyl-C(O)O, or two substituents are bound together to form a ring together with the carbon atoms to which they are attached and the two substituents together are —(CH$_2$)$_3$—; or b) heteroaryl, which heteroaryl is optionally substituted with 1 to 3 substituents independently selected from the group consisting of halogen, lower-alkyl and lower-alkoxy-lower-alkyl.

7. The compound according to claim 6, wherein R$^1$ and R$^2$, independently from each other, are phenyl which is substituted with a substituent in meta position with regard to the SO$_2$ moiety with a substituent selected from the group consisting of hydroxy and lower-alkyl-C(O)O.

8. The compound according to claim 7, wherein R$^1$ and R$^2$ are equal and are 3-hydroxy-phenyl or 3-acetyl-phenyl.

9. The compound according to claim 7, wherein R$^1$ and R$^2$, independently from each other, are thiophenyl which is optionally substituted with 1 to 2 substituents independently selected from lower-alkyl and lower-alkoxy-lower-alkyl.

10. The compound according to claim 9, wherein R$^1$ and R$^2$ are equal and are 4-methyl-thiophene-2-yl, 5-methyl-thiophene-3-yl, 5-methyl-thiophene-2-yl or 5(2-methoxy-ethyl)-4-methyl-thiophene-2-yl.

11. The compound according to claim 1, wherein m is 2 or 3.

12. The compound according to claim 1, wherein n is 2 or 3.

13. The compound according to claim 1, wherein m and n are 1, and L is cyclohexylene.

14. The compound according to claim 1, selected from the group consisting of
- N,N'-[hexane-1,6-diylbis(iminocarbonyl)]bis(3-chlorobenzenesulfonamide),
- N,N'-[heptane-1,7-diylbis(iminocarbonyl)]bis(3-chlorobenzene-sulfonamide),
- N,N'-[dithiobis(ethane-2,1-diyliminocarbonyl)]bis(3-chlorobenzenesulfonamide),
- N,N'-[octane-1,8-diylbis(iminocarbonyl)]bis(3-chlorobenzenesulfonamide),
- N,N'-[oxybis(propane-3,1-diyliminocarbonyl)]bis(3-chlorobenzenesulfonamide),
- N,N'-[pentane-1,5-diylbis(iminocarbonyl)]bis(3-chlorobenzenesulfonamide),
- N,N'-[cyclohexane-1,4-diylbis(methyleneiminocarbonyl)]bis(3-chlorobenzenesulfonamide) cis/trans mixture,
- N,N'-[hexane-1,6-diylbis(iminocarbonyl)]bis(3-methylbenzenesulfonamide),
- N,N'-[(3E)-hex-3-ene-1,6-diylbis(iminocarbonyl)]bis(3-chlorobenzenesulfonamide),
- N,N'-[hexane-1,6-diylbis(iminocarbonyl)]bis(3-fluorobenzenesulfonamide),
- N,N'-[hexane-1,6-diylbis(iminocarbonyl)]bis(3-aminobenzenesulfonamide),
- N,N'-[hexane-1,6-diylbis(iminocarbonyl)]bis(3-nitrobenzenesulfonamide),
- N,N'-[hexane-1,6-diylbis(iminocarbonyl)]bis(5-bromothiophene-2-sulfonamide),
- N,N'-[hexane-1,6-diylbisaminocarbonyl)]bis(5-chlorothiophene-2-sulfonamide),
- N,N'-[thiobis(ethane-2,1-diyliminocarbonyl)]bis(3-methylbenzenesulfonamide),
- N,N'-[dithiobis(ethane-2,1-diyliminocarbonyl)]bis(3-methylbenzenesulfonamide),
- N,N'-[hexane-1,6-diylbis(iminocarbonyl)]dithiophene-2-sulfonamide,
- N,N'-[pentane-1,5-diylbis(iminocarbonyl)]bis(3-methyl-benzenesulfonamide),
- N,N'-[heptane-1,7-diylbis(iminocarbonyl)]bis(3-methyl-benzenesulfonamide),
- N,N'-[octane-1,8-diylbis(iminocarbonyl)]bis(3-methyl-benzenesulfonamide),
- N,N'-[hexane-1,6-diylbisaminocarbonyl)]bis(5-methylthiophene-2-sulfonamide),
- dimethyl 5,5'-[hexane-1,6-diylbis(iminocarbonyliminosulfonyl)]dithiophene-2-carboxylate,
- N,N'-[hexane-1,6-diylbisaminocarbonyl)]bis(3-bromobenzenesulfonamide),
- N,N'-[hexane-1,6-diylbis(iminocarbonyl)]bis(3-hydroxybenzene-sulfonamide),
- N,N'-[hexane-1,6-diylbis(iminocarbonyl)]bis[5-hydroxymethyl)thiophene-2-sulfonamide,
- N,N-[hexane-1,6-diylbis(iminocarbonyl)]bis(5-bromofuran-2-sulfonamide),
- N,N'-[hexane-1,6-diylbisaminocarbonyl)]bis(5-methylfuran-2-sulfonamide),
- dimethyl 5,5'-[hexane-1,6-diylbisaminocarbonyliminosulfonyl)]di(2-furoate),
- 3,3'-[hexane-1,6-diylbis(iminocarbonyliminosulfonyl)]dibenzamide,
- N,N'-[hexane-1,6-diylbis(iminocarbonyl)]bis(5-cyanothiophene-2-sulfonamide,
- N,N'-[hexane-1,6-diylbis(iminocarbonyl)]bis(3-methoxybenzenesulfonamide),
- N,N'-[hexane-1,6-diylbis(iminocarbonyl)]bis(3-ethylbenzenesulfonamide),
- N,N'-[hexane-1,6-diylbis(iminocarbonyl)]bis(2,2-dimethyl-1,3-benzodioxole-5-sulfonamide),
- N,N'-[hexane-1,6-diylbis(iminocarbonyl)]bis(1,3-benzodioxole-5-sulfonamide),
- N,N'-[hexane-1,6-diylbisaminocarbonyl)]bis[5-(hydroxymethyl)furan-2-sulfonamide],
- N,N'-[hexane-1,6-diylbis(iminocarbonyl)]bis(3,4-dimethoxybenzenesulfonamide),
- N,N'-[hexane-1,6-diylbis(iminocarbonyl)]bis(3-fluoro-4-methylbenzenesulfonamide),
- N,N'-[hexane-1,6-diylbis(iminocarbonyl)]bis(3-chloro-4-methylbenzenesulfonamide),
- N,N'-[hexane-1,6-diylbis(iminocarbonyl)]bis(3,5-dimethylbenzenesulfonamide), and
- N,N'-[hexane-1,6-diylbis(iminocarbonyl)]bis(3,4-dihydroxybenzenesulfonamide), and pharmaceutically acceptable salts or esters thereof.

15. The compound according to claim 1, selected from the group consisting of
- N,N'-[hexane-1,6-diylbis(iminocarbonyl)]bis(3-chlorobenzene-sulfonamide),
- N,N'-[heptane-1,7-diylbis(iminocarbonyl)]bis(3-chlorobenzene-sulfonamide),
- N,N'-[hexane-1,6-diylbis(iminocarbonyl)]bis(3-methylbenzenesulfonamide),
- N,N'-[hexane-1,6-diylbisaminocarbonyl)]bis(3-fluorobenzenesulfonamide),
- N,N'-[thiobis(ethane-2,1-diyliminocarbonyl)]bis(3-methylbenzenesulfonamide),
- N,N'-[pentane-1,5-diylbis(iminocarbonyl)]bis(3-methylbenzenesulfonamide),
- N,N'-[heptane-1,7-diylbis(iminocarbonyl)]bis(3-methylbenzenesulfonamide),
- N,N'-[hexane-1,6-diylbisaminocarbonyl)]bis(5-methylthiophene-2-sulfonamide), and N,N'-[hexane-1,6-diylbis(iminocarbonyl)]bis(3-hydroxybenzenesulfonamide),
and pharmaceutically acceptable salts or esters thereof.

16. The compound according to claim 1, selected from the group consisting of
    N,N'-[hexane-1,6-diylbis(iminocarbonyl)]bis(3-cyclopropylbenzenesulfonamide),
    N,N'-[hexane-1,6-diylbis(iminocarbonyl)]bis[5-(2-methoxyethyl)-4-methylthiophene-2-sulfonamide],
    N,N'-[hexane-1,6-diylbis(iminocarbonyl)]bis(4-methylthiophene-2-sulfonamide),
    N,N'-[1,4-phenylenebis(methyleneiminocarbonyl)]bis(3-chlorobenzenesulfonamide),
    N,N'-[hexane-1,6-diylbis(iminocarbonyl)]bis(5-methylthiophene-3-sulfonamide),
    N,N'-[hexane-1,6-diylbis(iminocarbonyl)]bis(4-bromothiophene-2-sulfonamide),
    N,N'-[1,4-phenylenebis(methyleneiminocarbonyl)]bis(3-methylbenzenesulfonamide),
    N,N'-[hexane-1,6-diylbis(iminocarbonyl)]diindane-5-sulfonamide,
    N,N'-[1,4-phenylenebis(methyleneiminocarbonyl)]bis(3-chloro-4-fluorobenzenesulfonamide),
    N,N'-[hexane-1,6-diylbis(iminocarbonyl)]bis[3-(methoxymethyl)benzenesulfonamide],
    N,N'-[hexane-1,6-diylbis(iminocarbonyl)]bis[5-(methoxymethyl)thiophene-3-sulfonamide],
    3-methyl-N-({6[({[3-(trifluoromethyl)phenyl]sulfonyl}carbamoyl)amino]hexyl}carbamoyl)benzenesulfonamide,
    N,N'-[1,3-phenylenebis(methyleneiminocarbonyl)]bis(3-methylbenzenesulfonamide),
    N,N'-[1,4-phenylenebis(methyleneiminocarbonyl)]bis(4-fluoro-3-methylbenzenesulfonamide),
    N,N'-[1,4-phenylenebis(methyleneiminocarbonyl)]bis[4-fluoro-3-(trifluoromethyl)benzenesulfonamide],
    hexane-1,6-diylbis(iminocarbonyliminosulfonyl-3,1-phenylene)diacetate,
    N,N'-[hex-3-yne-1,6-diylbis(iminocarbonyl)]bis(3-methylbenzenesulfonamide),
    N,N'-[(2-chloro-1,4-phenylene)bis(methyleneiminocarbonyl)]bis(3-methylbenzenesulfonamide),
    N,N'-[hexane-1,6-diylbis(iminocarbonyl)]bis[5-(methoxymethyl)furan-3-sulfonamide],
    N,N'-[(2-fluoro-1,4-phenylene)bis(methyleneiminocarbonyl)]bis(3-methylbenzenesulfonamide),
    N,N'-[heptane-1,7-diylbis(iminocarbonyl)]bis(5-methylthiophene-3-sulfonamide),
    N,N'-[heptane-1,7-diylbis(iminocarbonyl)]bis[5-(methoxymethyl)thiophene-3-sulfonamide],
    N,N'-[heptane-1,7-diylbis(iminocarbonyl)]bis[5-(methoxymethyl)furan-3-sulfonamide],
    N,N'-[heptane-1,7-diylbis(iminocarbonyl)]bis(3-hydroxybenzenesulfonamide),
    N,N'-[(3E)-hex-3-ene-1,6-diylbis(iminocarbonyl)]bis(3-methylbenzenesulfonamide),
    N,N'-[(3E)-hex-3-ene-1,6-diylbis(iminocarbonyl)]bis(3-methylbenzenesulfonamide),
    N,N'-[heptane-1,7-diylbis(iminocarbonyl)]bis(5-methylthiophene-2-sulfonamide), and
    heptane-1,7-diylbis(iminocarbonyliminosulfonyl-3,1-phenylene)diacetate,
    and pharmaceutically acceptable salts or esters thereof.

17. The compound according to claim 1, selected from the group consisting of
    N,N'-[hexane-1,6-diylbis(iminocarbonyl)]bis[5-(2-methoxyethyl)-4-methylthiophene-2-sulfonamide],
    N,N'-[heptane-1,7-diylbisaminocarbonyl)]bis(5-methylthiophene-3-sulfonamide),
    N,N'-[heptane-1,7-diylbis(iminocarbonyl)]bis(3-hydroxybenzenesulfonamide),
    N,N'-[(3E)-hex-3-ene-1,6-diylbis(iminocarbonyl)]bis(3-methylbenzenesulfonamide),
    N,N'-[heptane-1,7-diylbis(iminocarbonyl)]bis(5-methylthiophene-2-sulfonamide), and
    heptane-1,7-diylbis(iminocarbonyliminosulfonyl-3,1-phenylene)diacetate,
    and pharmaceutically acceptable salts or esters thereof.

18. A process for the preparation of a compound according to claim 1, which process comprises the step of reacting a compound of formula (VI)

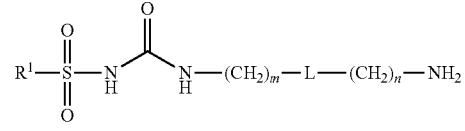

(VI)

with a compound of formula (VIII)

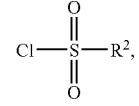

(VIII)

wherein $R^1$, $R^2$, L, m and n are as defined in any of claims 1 to 17.

19. A pharmaceutical composition, comprising a therapeutically effective amount of a compound according to claim 1 and a therapeutically inert carrier.

20. A method for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, comprising the step of administering a therapeutically effective amount of a compound according to claim 1 to a patient in need thereof.

* * * * *